(12) United States Patent
Kanai et al.

(10) Patent No.: US 11,066,372 B2
(45) Date of Patent: Jul. 20, 2021

(54) DEUTERATED BENZIMIDAZOLE COMPOUND AND MEDICAL USE THEREOF

(71) Applicant: Sumitomo Dainippon Pharma Co., Ltd., Osaka (JP)

(72) Inventors: Toshio Kanai, Osaka (JP); Kohei Iwamoto, Osaka (JP)

(73) Assignee: Sumitomo Dainippon Pharma Co., Ltd., Osaka (JP)

(*) Notice: Subject to any disclaimer, the term of this patent is extended or adjusted under 35 U.S.C. 154(b) by 81 days.

(21) Appl. No.: 16/494,128

(22) PCT Filed: Mar. 14, 2018

(86) PCT No.: PCT/JP2018/009873
§ 371 (c)(1),
(2) Date: Sep. 13, 2019

(87) PCT Pub. No.: WO2018/168894
PCT Pub. Date: Sep. 20, 2018

(65) Prior Publication Data
US 2020/0017450 A1 Jan. 16, 2020

(30) Foreign Application Priority Data
Mar. 15, 2017 (JP) .............................. JP2017050334

(51) Int. Cl.
| | | |
|---|---|---|
| *C07D 405/06* | (2006.01) | |
| *C07D 401/12* | (2006.01) | |
| *A61P 25/04* | (2006.01) | |
| *A61P 29/00* | (2006.01) | |
| *C07D 235/08* | (2006.01) | |
| *A61P 25/02* | (2006.01) | |
| *A61K 31/4184* | (2006.01) | |
| *A61K 31/4439* | (2006.01) | |
| *A61K 45/06* | (2006.01) | |

(52) U.S. Cl.
CPC ........ *C07D 235/08* (2013.01); *A61K 31/4184* (2013.01); *A61K 31/4439* (2013.01); *A61K 45/06* (2013.01); *A61P 25/02* (2018.01); *A61P 25/04* (2018.01); *A61P 29/00* (2018.01); *C07D 401/12* (2013.01); *C07D 405/06* (2013.01); *C07B 2200/05* (2013.01)

(58) Field of Classification Search
CPC ..... C07D 405/06; C07D 401/12; A61P 25/04; A61P 29/00
See application file for complete search history.

(56) References Cited

U.S. PATENT DOCUMENTS

| | | |
|---|---|---|
| 5,250,554 A | 10/1993 | Naka et al. |
| 2009/0137584 A1 | 5/2009 | Kato et al. |
| 2013/0225548 A1 | 8/2013 | Fujihara et al. |
| 2015/0152065 A1 | 6/2015 | Brookings et al. |
| 2017/0107211 A1 | 6/2017 | Komiya et al. |
| 2018/0170881 A1 | 6/2018 | Komiya et al. |

FOREIGN PATENT DOCUMENTS

| | | |
|---|---|---|
| JP | 04-009373 | 11/2007 |
| JP | 2009-536918 | 10/2009 |
| JP | 2014-114221 | 6/2014 |
| JP | 2015-519381 | 7/2015 |
| JP | 2018-052817 | 4/2018 |
| WO | WO 2012/057262 | 5/2014 |
| WO | WO 2016/117647 | 7/2016 |
| WO | WO 2017/043636 | 6/2018 |

OTHER PUBLICATIONS

Dib-Hajj et al., "The Na 1.7 Sodium Channel: from Molecule to Man," Nat Rev Neurosci., 2013, 14:49-62.
Hay et al., "Discovery and optimization of small-molecule ligands for the CBP/p300 bromodomains,"J Am Chem Soc, 2014, 136(26):9308-9319.
Minett et al., "Distinct Nav1.7-dependent Pain Sensations Require Different Sets of Sensory and Sympathetic Neurons," Nat Commun. 2012, 3:791.

(Continued)

*Primary Examiner* — Laura L Stockton
(74) *Attorney, Agent, or Firm* — Fish & Richardson P.C.

(57) ABSTRACT

The present invention relates to a medicament for treating or preventing a disease involving Na channel, for example, neuropathic pain, nociceptive pain, inflammatory pain, small-fiber neuropathy, erythromelalgia, paroxysmal extreme pain disorder, dysuria, or multiple sclerosis, comprising a compound of formula (I) wherein $R^{1a}$, $R^{1b}$, $R^{1c}$, and $R^{1d}$ are hydrogen, halogen, cyano, $C_{1-4}$ alkyl, $C_{1-4}$ alkoxy, etc., provided that at least one of $R^{1a}$, $R^{1b}$, $R^{1c}$ and $R^{1d}$ is the above $C_{6-10}$ aryl, $C_{6-10}$ aryloxy, etc., $R^2$ and $R^3$ are hydrogen, $C_{1-6}$ alkyl, $C_{3-10}$ cycloalkyl, etc., $R^4$ is hydrogen, $C_{1-6}$ alkyl, $C_{3-7}$ cycloalkyl, etc., m is 0, 1, or 2, L is $CR^7R^8$, $R^7$ and $R^8$ are hydrogen, hydroxy group, $C_{1-4}$ alkyl, $C_{1-4}$ alkoxy, etc., or a pharmaceutically acceptable salt thereof.

(I)

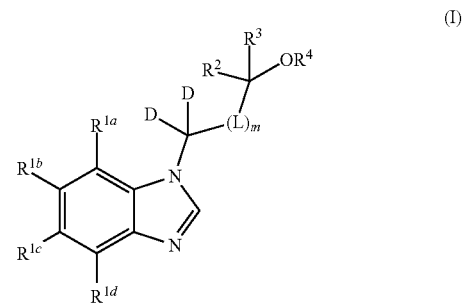

19 Claims, No Drawings

(56) References Cited

OTHER PUBLICATIONS

PCT International Preliminary Report on Patentability in International Appln. PCT/JP2018/009873, dated Sep. 17, 2019, 7 pages.
Takemura et al., "Copper-Catalyzed C-H Alkoxylation of Azoles," Organic letters, 2013, 15(4):844-847.

DEUTERATED BENZIMIDAZOLE COMPOUND AND MEDICAL USE THEREOF

TECHNICAL FIELD

The present invention relates to a medicament for treating or preventing a disease involving Na channel, particularly SCN9A (Nav 1.7), which comprises a novel compound having a benzimidazole skeleton or a pharmaceutically acceptable salt thereof as an active ingredient. In more detail, it relates to a medicament for treating or preventing a disease such as neuropathic pain, nociceptive pain, inflammatory pain, small-fiber neuropathy, erythromelalgia, paroxysmal extreme pain disorder, dysuria, and multiple sclerosis.

BACKGROUND ART

Voltage-dependent Na channel a subunit that forms pore is known to include 9 kinds at present. Recently, it has been evidenced that the subunit, particularly Nav 1.7 is broadly concerned in the signal transduction of acute and chronic pain.

SCN9A (Nav 1.7) is tetrodotoxin (TTX)-sensitive Na channel localized in the peripheral sensory nerve or sympathetic nerve, which is also referred to as NENA or PN1. Physiologically, Nav 1.7 channel functions to amplify a pain signal (i.e., generate a generator potential) at the sensory nerve ending. In the field of genetic investigation, it has been getting evident that a human whose SCN9A gene mutates to result in loss-of-function shows congenital insensitivity to pain. Reversely, in patients suffering from a severe orphan disease such as erythromelalgia and paroxysmal extreme pain disorder, it is observed that SCN9A gene mutates to result in gain-of-function. Furthermore, it has been reported that approximately 30% of patients suffering from small fiber neuropathy have genetic polymorphism to enhance Nav 1.7 function (Non-Patent Literature 1). And, it is suggested that Nav 1.7 channel function is directly concerned in the hyperexcitability of DRG neuron in patients suffering from pain since the expression level and activity increase in DRG neuron of model animals suffering from chronic pain, and neuropathic pain and inflammatory pain decrease in a knockout experiment (Non-Patent Literature 2).

Patent Literature 1 discloses a benzimidazole derivative represented by the following formula (A), but the compound has 2-((4-cyclopropylpyridin-2-yl)amino)isonicotinonitrile as an essential partial structure, which is different from the compound of the present invention. And, the invention described in Patent Literature 1 is directed to a Syk tyrosine kinase inhibitor, thus Patent Literature 1 does not disclose the present invention at all.

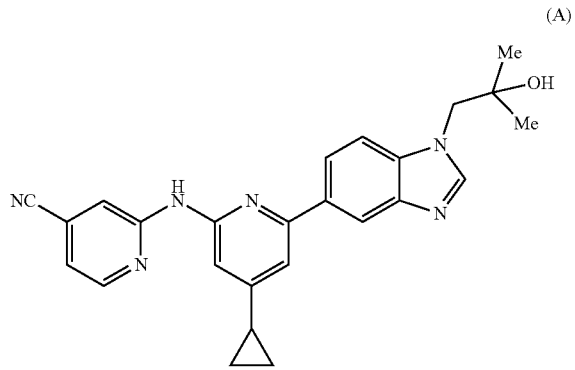 [SMILES: CC(C)(O)Cn1cnc2cc(-c3cc(C4CC4)cc(Nc4cc(C#N)ccn4)n3)ccc21]

(A)

Patent Literature 2 discloses a benzimidazole derivative represented by the following formula (B), which is directed to a Nav 1.7 inhibitor, but the compound has 2-(benzimidazol-1-yl)acetamide as an essential partial structure, which is different from the compound of the present invention.

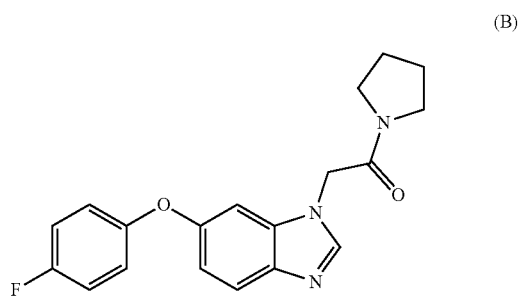 [SMILES: O=C(Cn1cnc2ccc(Oc3ccc(F)cc3)cc21)N1CCCC1]

(B)

PRIOR ART

Patent Literature

[Patent Literature 1] WO 2012/057262
[Patent Literature 2] WO 2016/117647

Non-Patent Literature

[Non-Patent Literature 1] Nat Rev Neurosci. 14: 49, 2013
[Non-Patent Literature 2] Nat Commun. 3: 791, 2012

SUMMARY OF INVENTION

Technical Problem

The purpose of the present invention may be to provide a medicament for treating or preventing a disease involving Nav 1.7, specifically such as neuropathic pain, nociceptive pain, inflammatory pain, small-fiber neuropathy, erythromelalgia, paroxysmal extreme pain disorder, dysuria, and multiple sclerosis.

Solution to Problem

The present inventors have conducted intensive studies in an attempt to solve the aforementioned problem and found that a compound having a benzimidazole ring mentioned below or a pharmaceutically acceptable salt thereof can inhibit the membrane potential change or the Na ion current itself via Na channel in Nav 1.7 gene expressing cell, i.e., the compound or a pharmaceutically acceptable salt thereof is a blocker having a inhibitory activity for Nav 1.7. In addition, the present inventors have found that the derivative is useful as a medicament for treating or preventing a disease such as neuropathic pain, nociceptive pain, inflammatory pain, small-fiber neuropathy, erythromelalgia, and paroxysmal extreme pain disorder, which resulted in the completion of the present invention. Accordingly, the present invention can provide a benzimidazole compound represented by the following formula (I) (hereinafter, also referred to as "compound represented by formula (I)" or "compound of formula (I)") or a pharmaceutically acceptable salt thereof, or a benzimidazole compound represented by the following formula (I') (hereinafter, also referred to as "compound represented by formula (I')" or "compound of formula (I')") or a pharmaceutically acceptable salt thereof (hereinafter, also referred to as "compound of the present invention").

The present invention can show as follows.
(Item 1)
A compound of formula (I):

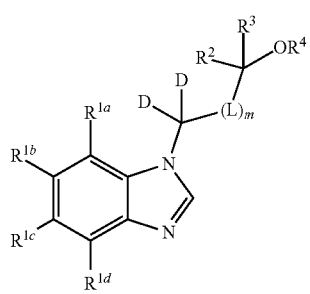

or a pharmaceutically acceptable salt thereof, wherein
$R^{1a}$, $R^{1b}$, $R^{1c}$, and $R^{1d}$ are independently hydrogen, halogen, cyano, $C_{1-4}$ alkyl, $C_{1-4}$ alkoxy, $C_{1-4}$ alkylamino (wherein the alkyl and the alkyl moiety in the alkoxy and the alkylamino may be independently substituted with 1 to 5 substituents selected independently from the group consisting of halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), $C_{3-7}$ cycloalkyl, $C_{3-7}$ cycloalkoxy, $C_{3-7}$ cycloalkylamino (wherein the cycloalkyl and the cycloalkyl moiety in the cycloalkoxy and the cycloalkylamino may be independently substituted with 1 to substituents selected independently from the group consisting of halogen, hydroxy group, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), $C_{6-10}$ aryl, $C_{6-10}$ aryloxy, 5- to 12-membered heteroaryl, or 5- to 12-membered heteroaryloxy (wherein the aryl and the aryl moiety in the aryloxy, and the heteroaryl and the heteroaryl moiety in the heteroaryloxy may be independently substituted with 1 to 5 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, 3- to 7-membered non-aromatic heterocyclyl optionally-substituted with 1 to 3 substituents selected independently from Substituent-group B, $C_{1-4}$ alkylthio optionally-substituted with 1 to 3 substituents selected independently from Substituent-group A, and $C_{1-4}$ alkylsulfonyl optionally-substituted with 1 to 3 substituents selected independently from Substituent-group A), provided that at least one of $R^{1a}$, $R^{1b}$, $R^{1c}$ and $R^{1d}$ is the above $C_{6-10}$ aryl, $C_{6-10}$ aryloxy, 5- to 12-membered heteroaryl or 5- to 12-membered heteroaryloxy, $R^2$ and $R^3$ are independently hydrogen, $C_{1-6}$ alkyl (which may be independently substituted with 1 to 5 substituents selected independently from the group consisting of cyano, halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), or $C_{3-10}$ cycloalkyl, $R^4$ is hydrogen, $C_{1-6}$ alkyl (which may be substituted with 1 to 3 substituents selected independently from the group consisting of halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), or $C_{3-7}$ cycloalkyl (which may be independently substituted with 1 to 3 substituents selected independently from the group consisting of halogen, hydroxy group, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), m is 0, 1, or 2, L is $CR^7R^8$ provided that when m is 2, each $CR^7R^8$ is independently the same or different, $R^7$ and $R^8$ are independently hydrogen, hydroxy group, $C_{1-4}$ alkyl, $C_{1-4}$ alkoxy (wherein the alkyl and the alkyl moiety in the alkoxy may be independently substituted with 1 to 3 substituents selected independently from the group consisting of halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), $C_{3-7}$ cycloalkyl, or $C_{3-7}$ cycloalkoxy (wherein the cycloalkyl and the cycloalkyl moiety in the cycloalkoxy may be independently substituted with 1 to 3 substituents selected independently from the group consisting of halogen, hydroxy group, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), or in $R^2$, $R^3$ and —$OR^4$, $R^2$ and $R^3$ may be combined together with the carbon atom to which they are attached to form the following group of formula (II) with —$OR^4$

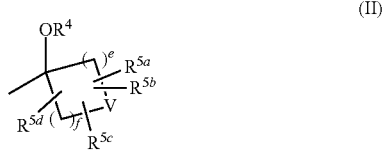
(II)

in formula (II), e and f are independently 1, 2 or 3, $R^4$ is as defined above, V is single bond or oxygen atom, $R^{5a}$, $R^{5b}$, $R^{5c}$, and $R^{5d}$ are independently hydrogen, halogen, hydroxy group, $C_{1-4}$ alkyl, or $C_{1-4}$ alkoxy, wherein the alkyl and the alkyl moiety in the alkoxy may be independently substituted with 1 to 3 substituents selected independently from the group consisting of halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, Substituent-group A is independently halogen, hydroxy group, $C_{1-4}$ alkoxy, $C_{3-7}$ cycloalkyl, or $C_{3-7}$ cycloalkoxy, Substituent-group B is independently halogen, hydroxy group, $C_{1-4}$ alkyl, $C_{1-4}$ alkoxy, $C_{3-7}$ cycloalkyl, or $C_{3-7}$ cycloalkoxy, and further any 1 to 6 hydrogen atoms in the compound of formula (I) may be replaced with deuterium atoms.

(Item 1-1)

A compound of formula (I'):

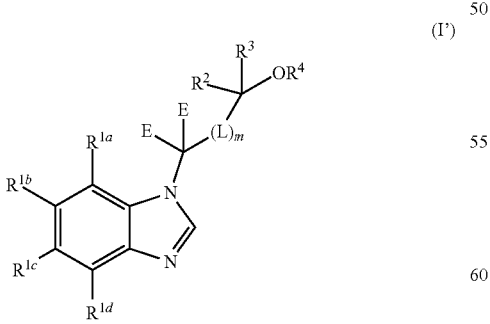
(I')

or a pharmaceutically acceptable salt thereof, wherein

E is hydrogen, $R^{1a}$, $R^{1b}$, $R^{1c}$, and $R^{1d}$ are independently hydrogen, halogen, cyano, $C_{1-4}$ alkyl, $C_{1-4}$ alkoxy, $C_{1-4}$ alkylamino (wherein the alkyl and the alkyl moiety in the alkoxy and the alkylamino may be independently substituted with 1 to 5 substituents selected independently from the group consisting of halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), $C_{3-7}$ cycloalkyl, $C_{3-7}$ cycloalkoxy, $C_{3-7}$ cycloalkylamino (wherein the cycloalkyl and the cycloalkyl moiety in the cycloalkoxy and the cycloalkylamino may be independently substituted with 1 to substituents selected independently from the group consisting of halogen, hydroxy group, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), $C_{6-10}$ aryl, $C_{6-10}$ aryloxy, 5- to 12-membered heteroaryl, or 5- to 12-membered heteroaryloxy (wherein the aryl and the aryl moiety in the aryloxy, and the heteroaryl and the heteroaryl moiety in the heteroaryloxy may be independently substituted with 1 to 5 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, 3- to 7-membered non-aromatic heterocyclyl optionally-substituted with 1 to 3 substituents selected independently from Substituent-group B, $C_{1-4}$ alkylthio optionally-substituted with 1 to 3 substituents selected independently from Substituent-group A, and $C_{1-4}$ alkylsulfonyl optionally-substituted with 1 to 3 substituents selected independently from Substituent-group A), provided that at least one of $R^{1a}$, $R^{1b}$, $R^{1c}$ and $R^{1d}$ is the above $C_{6-10}$ aryl, $C_{6-10}$ aryloxy, 5- to 12-membered heteroaryl or 5- to 12-membered heteroaryloxy, $R^2$ and $R^3$ are independently hydrogen, $C_{1-6}$ alkyl (which may be independently substituted with 1 to 5 substituents selected independently from the group consisting of cyano, halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), or $C_{3-10}$ cycloalkyl, $R^4$ is hydrogen, $C_{1-6}$ alkyl (which may be substituted with 1 to 3 substituents selected independently from the group consisting of halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), or $C_{3-7}$ cycloalkyl (which may be independently substituted with 1 to 3 substituents selected independently from the group consisting of halogen, hydroxy group, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), m is 0, 1, or 2, L is $CR^7R^8$ provided that when m is 2, each $CR^7R^8$ is independently the same or different, $R^7$ and $R^8$ are independently hydrogen, hydroxy group, $C_{1-4}$ alkyl, $C_{1-4}$ alkoxy (wherein the alkyl and the alkyl moiety in the alkoxy may be independently substituted with 1 to 3 substituents selected independently from the group consisting of halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), $C_{3-7}$ cycloalkyl, or $C_{3-7}$ cycloalkoxy (wherein the cycloalkyl and the cycloalkyl moiety in the cycloalkoxy may be independently substituted with 1 to 3 substituents selected independently from the group consisting of halogen, hydroxy group, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), or in $R^2$, $R^3$ and —$OR^4$, $R^2$ and $R^3$ may be combined together with the carbon atom to which they are attached to form the following group of formula (II) with —$OR^4$

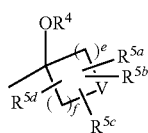

(II)

in formula (II), e and f are independently 1, 2 or 3, $R^4$ is as defined above, V is single bond or oxygen atom, $R^{5a}$, $R^{5b}$, $R^{5c}$, and $R^{5d}$ are independently hydrogen, halogen, hydroxy group, $C_{1-4}$ alkyl, or $C_{1-4}$ alkoxy, wherein the alkyl and the alkyl moiety in the alkoxy may be independently substituted with 1 to 3 substituents selected independently from the group consisting of halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, Substituent-group A is independently halogen, hydroxy group, $C_{1-4}$ alkoxy, $C_{3-7}$ cycloalkyl, or $C_{3-7}$ cycloalkoxy, Substituent-group B is independently halogen, hydroxy group, $C_{1-4}$ alkyl, $C_{1-4}$ alkoxy, $C_{3-7}$ cycloalkyl, or $C_{3-7}$ cycloalkoxy, provided that any 1 to 8 hydrogen atoms in the compound of formula (I') are replaced with deuterium atoms.

(Item 1-2)

The compound of Item 1 or Item 1-1 or a pharmaceutically acceptable salt thereof, provided that the following compounds having deuterium atom instead of the predefined hydrogen atom are excluded:

6-[6-chloro-2-(morpholin-4-yl)pyrimidin-4-yl]-1-(2-methoxyethyl)-1H-benzimidazole, 2-[5-(3,5-dimethyl-1,2-oxazol-4-yl)-1H-benzimidazol-1-yl]ethanol, 2-{5-[5-(tetrahydrofuran-3-yl)-4H-1,2,4-triazol-3-yl]-1H-benzimidazol-1-yl}ethanol, 2-{5-[3-(2-methoxyethyl)-1-(2,2,2-trifluoroethyl)-1H-1,2,4-triazol-5-yl]-1H-benzimidazol-1-yl}ethanol, 2-{5-[3-methyl-1-(l-methylpiperidin-4-yl)-1H-1,2,4-triazol-5-yl]-1H-benzimidazol-1-yl}ethanol, 2-butyl-6-[1-(2-hydroxyethyl)-1H-benzimidazol-6-yl]-3,4-dihydropyrrolo[1,2-a]pyrazin-1(2H)-one, 6-[1-(2-hydroxyethyl)-1H-benzimidazol-6-yl]-2-(3-methylbutyl)-3,4-dihydropyrrolo[1,2-a]pyrazin-1(2H)-one, 2-{5-[l-(2-hydroxyethyl)-1H-benzimidazol-5-yl]-1H-1,2,4-triazol-1-yl}ethanol, 6-(2-chlorophenyl)-1-(2-hydroxyethyl)-1H-benzimidazole-7-carbonitrile, 2-chloro-6-{7-fluoro-1-[(1S,3S)-3-methoxycyclohexyl]-1H-benzimidazol-5-yl}-9-(tetrahydro-2H-pyran-2-yl)-9H-purine, and 2-{5-[2-(tetrahydrofuran-3-yl)-1H-imidazol-1-yl]-1H-benzimidazol-1-yl}ethanol.

(Item 2)

The compound of Item 1 or a pharmaceutically acceptable salt thereof, wherein $R^{1a}$, $R^{1b}$, $R^{1c}$, and $R^{1d}$ are independently, hydrogen, halogen, cyano, $C_{1-4}$ alkyl, $C_{1-4}$ alkoxy (wherein the alkyl and the alkyl moiety in the alkoxy may be independently substituted with 1 to 3 the same or different halogen atoms), $C_{6-10}$ aryl, $C_{6-10}$ aryloxy, 5- to 12-membered heteroaryl, or 5- to 12-membered heteroaryloxy (wherein the aryl and the aryl moiety in the aryloxy, and the heteroaryl and the heteroaryl moiety in the heteroaryloxy may be independently substituted with 1 to 3 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, and $C_{1-4}$ alkylsulfonyl optionally-substituted with 1 to 3 substituents selected independently from Substituent-group A).

(Item 3)

The compound of Item 1 or 2 or a pharmaceutically acceptable salt thereof, wherein $R^{1a}$, $R^{1b}$, $R^{1c}$, and $R^{1d}$ are independently, hydrogen, $C_{6-10}$ aryl, $C_{6-10}$ aryloxy, 5- to 12-membered heteroaryl, or 5- to 12-membered heteroaryloxy, wherein the aryl and the aryl moiety in the aryloxy, and the heteroaryl and the heteroaryl moiety in the heteroaryloxy may be independently substituted with 1 to 3 substituents selected independently from the group consisting of halogen, $C_{1-4}$ alkyl optionally-substituted with 1 to 3 substituents selected independently from Substituent-group A, and $C_{1-4}$ alkoxy optionally-substituted with 1 to 3 substituents selected independently from Substituent-group A.

(Item 4)

The compound of any one of Items 1 to 3 or a pharmaceutically acceptable salt thereof, wherein $R^{1a}$ and $R^{1d}$ are hydrogen.

(Item 5)

The compound of any one of Items 1 to 4 or a pharmaceutically acceptable salt thereof, wherein $R^{1b}$ or $R^{1c}$ is $C_{6-10}$ aryl, $C_{6-10}$ aryloxy, 5- to 12-membered heteroaryl, or 5- to 12-membered heteroaryloxy (wherein the aryl and the aryl moiety in the aryloxy, and the heteroaryl and the heteroaryl moiety in the heteroaryloxy may be independently substituted with 1 to 3 substituents selected independently from the group consisting of halogen, $C_{1-4}$ alkyl optionally-substituted with 1 to 3 substituents selected independently from Substituent-group A, and $C_{1-4}$ alkoxy optionally-substituted with 1 to 3 substituents selected independently from Substituent-group A).

(Item 6)

The compound of any one of Items 1 to 5 or a pharmaceutically acceptable salt thereof, wherein $R^{1a}$, $R^{1c}$, and $R^{1d}$ are hydrogen.

(Item 7)

The compound of any one of Items 1 to 6 or a pharmaceutically acceptable salt thereof, wherein $R^{1b}$ is $C_{6-10}$ aryl, $C_{6-10}$ aryloxy, 5- to 12-membered heteroaryl, or 5- to 12-membered heteroaryloxy (wherein the aryl and the aryl moiety in the aryloxy, and the heteroaryl and the heteroaryl moiety in the heteroaryloxy may be independently substituted with 1 to 3 substituents selected independently from the group consisting of halogen, $C_{1-4}$ alkyl optionally-substituted with 1 to 3 substituents selected independently from Substituent-group A, and $C_{1-4}$ alkoxy optionally-substituted with 1 to 3 substituents selected independently from Substituent-group A).

(Item 8)

The compound of any one of Items 1 to 7 or a pharmaceutically acceptable salt thereof, wherein $R^2$ and $R^3$ are independently hydrogen or $C_{1-6}$ alkyl which may be independently substituted with 1 to 5 substituents selected independently from the group consisting of cyano, halogen, hydroxy group, and $C_{1-4}$ alkoxy optionally-substituted with 1 to 3 substituents selected independently from Substituent-group A, provided that both of $R^2$ and $R^3$ are not hydrogen, or $R^2$ and $R^3$ may be combined together with the carbon atom to which they are attached to form the following group of formula (IIa) with —$OR^4$

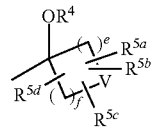

(IIa)

in formula (IIa), e and f are independently 1 or 2, $R^4$ and V are as defined in Item 1, and $R^{5a}$, $R^{5b}$, $R^{5c}$, and $R^{5d}$ are independently hydrogen or halogen.

(Item 9)

The compound of any one of Items 1 to 8 or a pharmaceutically acceptable salt thereof, wherein $R^2$ and $R^3$ are independently $C_{1-6}$ alkyl optionally-substituted with 1 to 5 the same or different halogen atoms, or $R^2$ and $R^3$ may be combined together with the carbon atom to which they are attached to form the following group of formula (IIb) with —$OR^4$

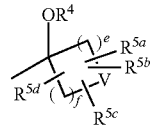

(IIb)

in formula (IIb), e and f are 1, $R^4$ is hydrogen,

V is oxygen atom, $R^{5a}$, $R^{5b}$, $R^{5c}$, and $R^{5d}$ are independently hydrogen or halogen.

(Item 10)

The compound of any one of Items 1 to 9 or a pharmaceutically acceptable salt thereof, wherein $R^2$ and $R^3$ are independently hydrogen or $C_{1-6}$ alkyl optionally-substituted with 1 to 5 the same or different halogen atoms, and $R^2$ and $R^3$ are not combined together with the carbon atom to which they are attached to form a ring.

(Item 11)

The compound of any one of Items 1 to 9 or a pharmaceutically acceptable salt thereof, wherein $R^2$ and $R^3$ may be combined together with the carbon atom to which they are attached to form the following group of formula (IIb) with —$OR^4$

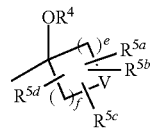

(IIb)

in formula (IIb), e and f are 1, $R^4$ is hydrogen,

V is oxygen atom, $R^{5a}$, $R^{5b}$, $R^{5c}$, and $R^{5d}$ are independently hydrogen or halogen.

(Item 12)

The compound of any one of Items 1 to 11 or a pharmaceutically acceptable salt thereof, wherein $R^4$ is hydrogen, $C_{1-4}$ alkyl optionally-substituted with 1 to 3 the same or different halogen atoms, or $C_{3-7}$ cycloalkyl which may be substituted with 1 to 3 substituents selected independently from the group consisting of halogen, hydroxy group, and $C_{1-4}$ alkoxy optionally-substituted with 1 to 3 substituents selected independently from Substituent-group A.

(Item 13)

The compound of any one of Items 1 to 12 or a pharmaceutically acceptable salt thereof, wherein $R^4$ is hydrogen.

(Item 14)

The compound of any one of Items 1 to 13 or a pharmaceutically acceptable salt thereof, wherein $R^7$ and $R^8$ are independently hydrogen or $C_{1-4}$ alkyl which may be substituted with 1 to 3 substituents selected independently from the group consisting of halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, and m is 0 or 1.

(Item 15)

The compound of any one of Items 1 to 14 or a pharmaceutically acceptable salt thereof, wherein $R^7$ and $R^8$ are hydrogen, and m is 0 or 1.

(Item 16)

The compound of Item 1 or a pharmaceutically acceptable salt thereof, which is selected from the following compounds:

Example 1

6-(4-fluorophenoxy)-1H-benzimidazol-1-yl]-2-methyl (1,1-$^2H_2$) propan-2-ol,

Example 2

2-methyl-1-(6-{[5-(trifluoromethyl)pyridin-2-yl]oxy}-1H-benzimidazol-1-yl) (1,1-$^2H_2$)propan-2-ol, Example 3

4-[6-(4-chlorophenoxy)-1H-benzimidazol-1-yl]-2-methyl (4, 4-$^2H_2$) butan-2-ol, Example 4

3-[{6-[4-(trifluoromethoxy)phenoxy]-1H-benzimidazol-1-yl}($^2H_2$)methyl]oxetan-3-ol, and Example 5

3-[{6-[2-methoxy-4-(trifluoromethyl)phenyl]-1H-benzimidazol-1-yl}($^2H_2$)methyl]oxetan-3-ol.

(Item 17)

The compound of Item 1 or a pharmaceutically acceptable salt thereof, which is selected from the following compounds:

Example 1

6-(4-fluorophenoxy)-1H-benzimidazol-1-yl]-2-methyl(1,1-$^2H_2$) propan-2-ol,

Example 2

2-methyl-1-(6-{[5-(trifluoromethyl)pyridin-2-yl]oxy}-1H-benzimidazol-1-yl) (1,1-$^2H_2$)propan-2-ol, and Example 3

4-[6-(4-chlorophenoxy)-1H-benzimidazol-1-yl]-2-methyl (4, 4-$^2H_2$) butan-2-ol.

(Item 18)

The compound of Item 1 or a pharmaceutically acceptable salt thereof, which is selected from the following compounds:

Example 4

3-[{6-[4-(trifluoromethoxy)phenoxy]-1H-benzimidazol-1-yl}($^2H_2$)methyl]oxetan-3-ol, and Example 5

3-[{6-[2-methoxy-4-(trifluoromethyl)phenyl]-1H-benzimidazol-1-yl}($^2H_2$)methyl]oxetan-3-ol.

(Item 19)

A pharmaceutical combination comprising the compound of any one of Items 1 to 18 or a pharmaceutically acceptable salt thereof.

(Item 20)

A medicament for treating a disease involving Nav 1.7 (SCN9A), comprising the compound of any one of Items 1 to 18 or a pharmaceutically acceptable salt thereof as an active ingredient.

(Item 21)

A medicament for treating neuropathic pain, nociceptive pain, inflammatory pain, small-fiber neuropathy, erythromelalgia, paroxysmal extreme pain disorder, dysuria, or multiple sclerosis, which comprises the compound of any one of Items 1 to 18 or a pharmaceutically acceptable salt thereof as an active ingredient.

(Item 22)

A pharmaceutical combination comprising the compound of any one of Items 1 to 18 or a pharmaceutically acceptable salt thereof, and at least one drug selected from the group consisting of an antiepileptic agent, an antidepressive agent, a narcotic analgesic, an anti-inflammatory agent, a reductase inhibitor, and a prostaglandin derivative drug.

(Item 23)

Use of the compound of any one of Items 1 to 18 or a pharmaceutically acceptable salt thereof in the manufacture of a medicament for treating neuropathic pain, nociceptive pain, inflammatory pain, small-fiber neuropathy, erythromelalgia, paroxysmal extreme pain disorder, dysuria, or multiple sclerosis.

(Item 24)

A method for treating neuropathic pain, nociceptive pain, inflammatory pain, small-fiber neuropathy, erythromelalgia, paroxysmal extreme pain disorder, dysuria, or multiple sclerosis, which comprises administering a therapeutically effective amount of the compound of any one of Items 1 to 18 or a pharmaceutically acceptable salt thereof to a mammal in need thereof.

(Item 25)
The embodiments of Items 2 to 24, wherein the compounds defined in Items 2 to 24 do not include the compounds excluded in Item 1-2.

Effect of Invention

The present invention provides a Nav 1.7 blocker comprising a novel benzimidazole compound or a pharmaceutically acceptable salt thereof. The compounds of the present invention are useful as a medicament for treating or preventing a disease involving Nav 1.7 (SCN9A), namely, the compounds are applicable to a patient suffering from neuropathic pain, nociceptive pain, inflammatory pain, small-fiber neuropathy, erythromelalgia, paroxysmal extreme pain disorder, and the like. In addition, the present invention provides an excellent metabolically-stable compound by introducing deuterium atom at specific position(s) of the compound.

DESCRIPTION OF EMBODIMENTS

Hereinafter, the present invention is explained in detail. In the description, the number of carbon atoms in the definition of "substituents" can indicates, for example, "$C_{1-6}$". The specific definition "$C_{1-6}$ alkyl" means an alkyl group having 1 to 6 carbon atoms. In the present description, a substituent group which is not accompanied with "optionally-substituted" or "substituted" means an "unsubstituted" substituent group. For example, "$C_{1-6}$ alkyl" means "unsubstituted $C_{1-6}$ alkyl".

The substituent groups in the present description may be sometimes expressed without the term "group". In case that "optionally-substituted" is used in the definition of substituent groups, the number of the substituting groups is not limited as long as the substitutions are available, i.e., it is one or more. It means that the possible number of substituting groups is the substitution-available number on carbon atoms or carbon-nitrogen atoms in a substituent group which are acceptable for substitution. Unless otherwise specified, the definition of each substituent group also extends over the case of partially-including the substituent group or the case of the substituent group substituting another substituent group.

Unless otherwise specified, the binding site of substituent groups is not limited as long as the site is available to be bound.

The "halogen" includes, for example, fluorine, chlorine, bromine, and iodine, preferably fluorine and chlorine.

The "$C_{1-2}$ alkyl" means a saturated hydrocarbon group having 1 to 2 carbon atoms, the "$C_{1-3}$ alkyl" means a saturated straight or branched chain hydrocarbon group having 1 to 3 carbon atoms, the "$C_{1-4}$ alkyl" means a saturated straight or branched chain hydrocarbon group having 1 to 4 carbon atoms, and the "$C_{1-6}$ alkyl" means a saturated straight or branched chain hydrocarbon group having 1 to 6 carbon atoms. The "$C_{1-2}$ alkyl" includes, for example, methyl and ethyl; the "$C_{1-3}$ alkyl" includes, for example, propyl and isopropyl, besides the above alkyl; the "$C_{1-4}$ alkyl" includes, for example, butyl, isobutyl, sec-butyl, and tert-butyl, besides the above alkyl; and the "$C_{1-6}$ alkyl" includes, for example, pentyl, isopentyl, neopentyl, 1-ethylpropyl, hexyl, and a structural isomer thereof, besides the above alkyl. Preferred examples of the "$C_{1-6}$ alkyl" or "$C_{1-4}$ alkyl" include "$C_{1-3}$ alkyl", and more preferably methyl and ethyl.

The "$C_{3-7}$ cycloalkyl" means a non-aromatic cyclic hydrocarbon group (i.e., saturated hydrocarbon group and partially-unsaturated hydrocarbon group) having 3 to 7 carbon atoms, and the "$C_{3-10}$ cycloalkyl" means a non-aromatic cyclic hydrocarbon group (i.e., saturated hydrocarbon group and partially-unsaturated hydrocarbon group) having 3 to 10 carbon atoms. The "$C_{3-7}$ cycloalkyl" and the "$C_{3-10}$ cycloalkyl" also include a bridged one. The "$C_{3-7}$ cycloalkyl" includes, for example, cyclopropyl, cyclobutyl, cyclopentyl, cyclohexyl, cyclopentenyl, cyclohexenyl, and cycloheptyl. The "$C_{3-10}$ cycloalkyl" includes, for example, cyclooctyl and adamantyl, besides the above, preferably, "$C_{3-7}$ cycloalkyl".

The "$C_{3-7}$ cycloalkyl" and the "$C_{3-10}$ cycloalkyl" also include a bi-cyclic condensed ring in which the "$C_{3-7}$ cycloalkyl" and "$C_{3-10}$ cycloalkyl" are fused with benzene or a 5- or 6-membered ring having one heteroatom selected from nitrogen, sulfur, or oxygen atom, or two or more (for example, 2 to 4) the same or different heteroatoms thereof (for example, "5- or 6-membered mono-cyclic heteroaryl" mentioned below, and 5- or 6-membered ring in "3- to 7-membered non-aromatic heterocyclyl" mentioned below), respectively. Examples of the bi-cyclic condensed ring include groups of the following formulae.

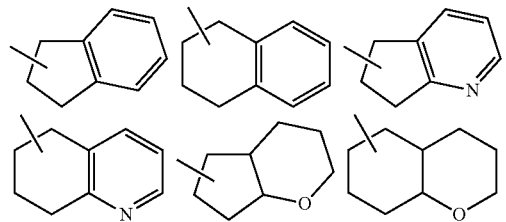

The "$C_{6-10}$ aryl" used herein means an aromatic hydrocarbon group having 6-10 carbon atoms, preferably phenyl. The "$C_{6-10}$ aryl" includes, for example, phenyl, 1-naphthyl, and 2-naphthyl.

The "$C_{6-10}$ aryl" also includes a condensed ring in which "phenyl" is fused with a 5- or 6-membered ring having one heteroatom selected from nitrogen, sulfur, or oxygen atom, or two or more (for example, 2 to 4) the same or different heteroatoms thereof (for example, "5- or 6-membered mono-cyclic heteroaryl" mentioned below, and 5- or 6-membered ring in "3- to 7-membered non-aromatic heterocyclyl" mentioned below), or a 5- to 7-membered cycloalkyl ring (for example, cyclopentane, cyclohexane and cycloheptane). Examples of the condensed ring include groups of the following formulae.

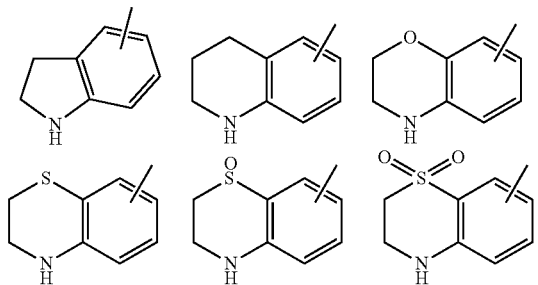

-continued

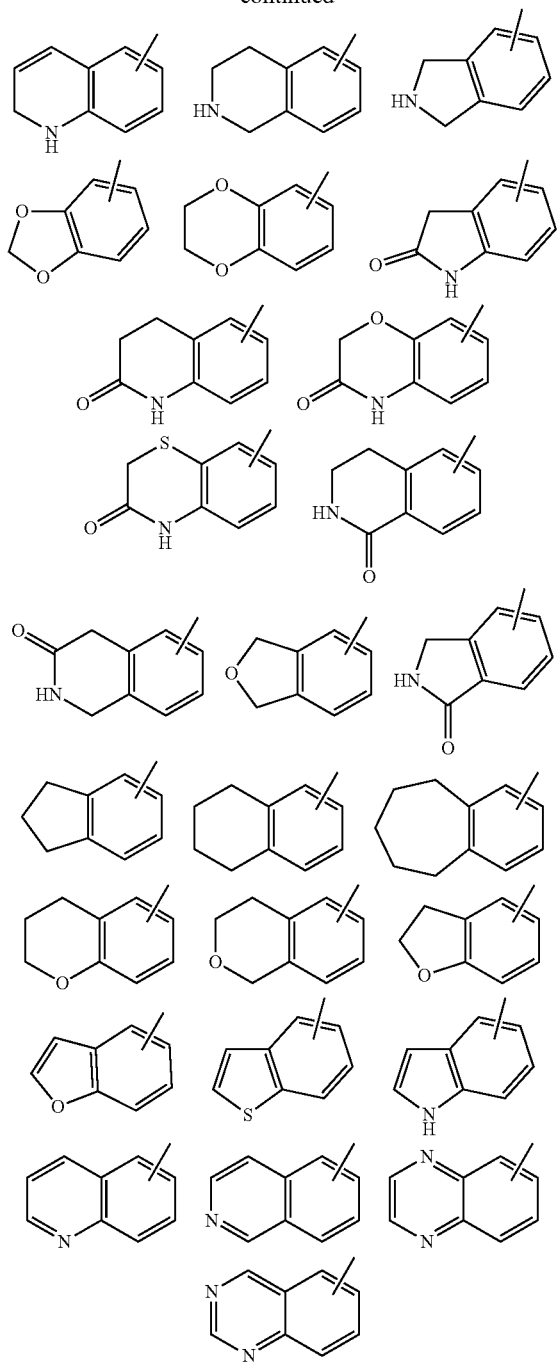

The "5- to 12-membered heteroaryl" means a 5- to 12-membered mono- or multiple-cyclic aromatic group having one 5 heteroatom selected from nitrogen, sulfur, or oxygen atom, or two or more (for example, 2 to 4) the same or different heteroatoms thereof, besides carbon atoms as the ring atoms, preferably, "5- or 6-membered mono-cyclic heteroaryl". The "5- or 6-membered mono-cyclic heteroaryl" means a 5- or 6-membered mono-cyclic aromatic group within the "5- to 12-membered heteroaryl".

The multiple-cyclic heteroaryl in the "5- to 12-membered heteroaryl" includes, for example, a condensed ring in which two the same or different mono-cyclic heteroaryls are fused, or a mono-cyclic heteroaryl and an aromatic ring (for example, benzene) or a non-aromatic ring (for example, cyclohexane) are fused.

The "5- to 12-membered heteroaryl" includes, for example, groups of the formulae shown below. Preferably, the "5- to 12-membered heteroaryl" includes pyrazolyl, imidazolyl, pyridyl, pyrimidinyl, pyrazinyl, and pyridazinyl. Another embodiment includes, preferably, benzofuranyl in which the binding site is on the heteroaryl (furan) ring, pyridyl, pyrimidinyl, pyrazinyl, and pyridazinyl. Examples of the "5- or 6-membered mono-cyclic heteroaryl" include mono-cyclic groups out of the groups of the following formulae.

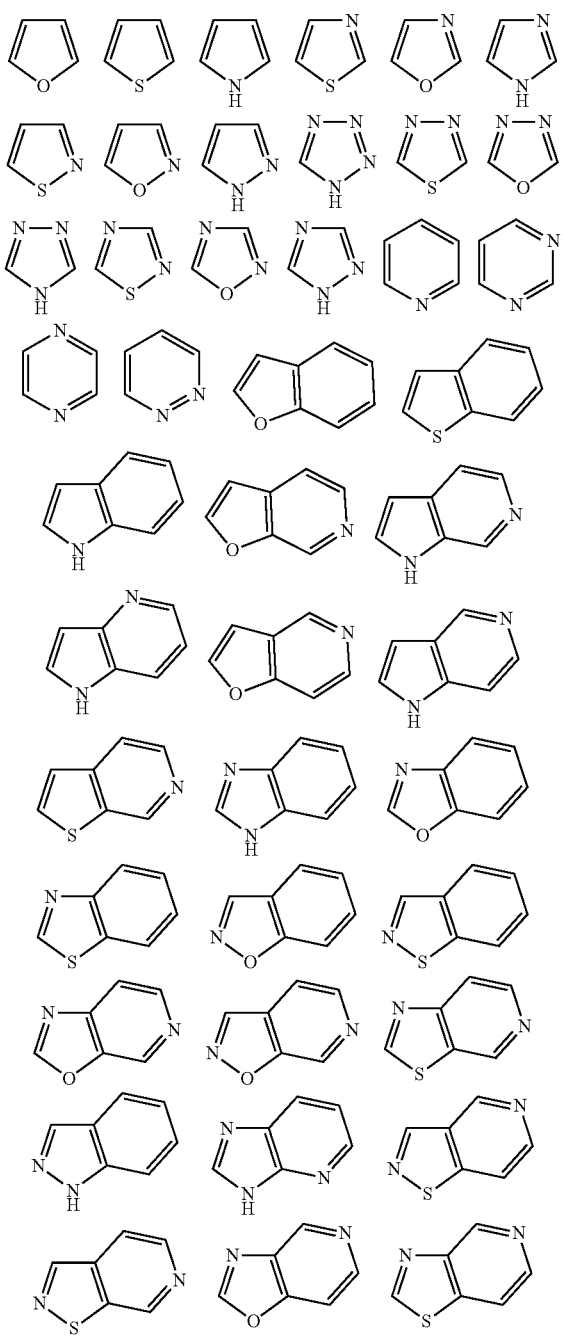

-continued

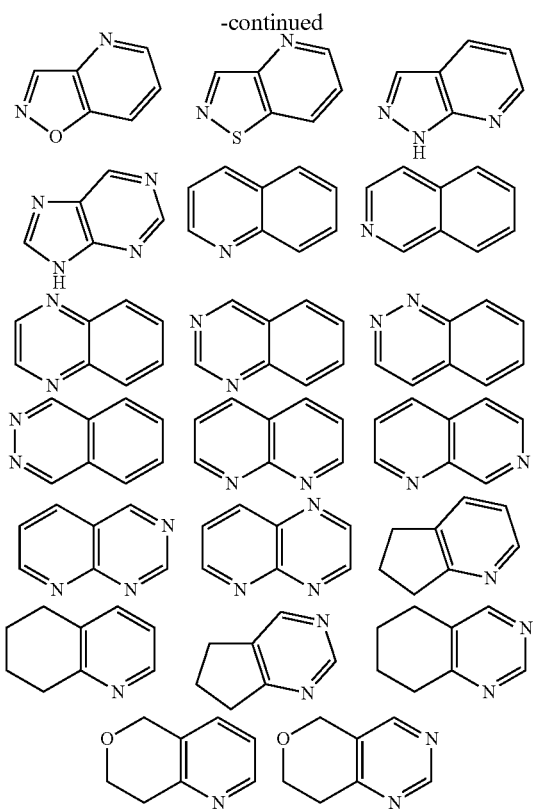

The "3- to 7-membered non-aromatic heterocyclyl" means 3- to 7-membered cyclic group having one heteroatom selected from nitrogen, oxygen, or sulfur atom, or two or more (for example, 2 to 4, preferably 2 to 3) the same or different heteroatoms thereof, besides carbon atoms as the ring atoms. The heterocyclyl is non-aromatic, which may be a saturated one or a partially-unsaturated one. Preferred one thereof is a saturated heterocyclyl, more preferably 5- or 6-membered saturated heterocyclyl. The "3- to 7-membered non-aromatic heterocyclyl" includes, for example, oxetanyl, azetidinyl, pyranyl, tetrahydrofuryl, pyrrolidinyl, pyrazolidinyl, imidazolidinyl, piperidinyl, morpholinyl, thiomorpholinyl, dioxothiomorpholinyl, hexamethyleneiminyl, oxazolidinyl, thiazolidinyl, imidazolidinyl, oxoimidazolidinyl, dioxoimidazolidinyl, oxo-oxazolidinyl, dioxo-oxazolidinyl, dioxothiazolidinyl, tetrahydropyranyl, and tetrahydropyridinyl, and preferably pyranyl, tetrahydrofuryl, pyrrolidinyl, piperidinyl, and morpholinyl.

The "3- to 7-membered non-aromatic heterocyclyl" also includes a condensed ring in which the 3- to 7-membered non-aromatic heterocyclyl is fused with benzene or a 6-membered heteroaryl (for example, pyridine, pyrimidine or pyridazine). The examples thereof include dihydroindolyl, dihydroisoindolyl, dihydropurinyl, dihydrothiazolopyrimidinyl, dihydrobenzodioxanyl, isoindolinyl, indazolyl, pyrrolopyridinyl, tetrahydroquinolinyl, decahydroquinolinyl, tetrahydroisoquinolinyl, decahydroisoquinolinyl, tetrahydronaphthyridinyl, and tetrahydropyridoazepinyl.

The "$C_{1-2}$ alkoxy" means oxy group substituted with the above "$C_{1-2}$ alkyl", and the "$C_{1-4}$ alkoxy" means oxy group substituted with the above "$C_{1-4}$ alkyl". The "$C_{1-2}$ alkoxy" includes, for example, methoxy and ethoxy, and the "$C_{1-4}$ alkoxy" includes, for example, propoxy, isopropoxy, butoxy, isobutoxy, sec-butoxy, and tert-butoxy, besides the above examples. Preferably, the "$C_{1-4}$ alkoxy" includes methoxy, ethoxy, and isopropoxy.

The "$C_{3-7}$ cycloalkoxy" means oxy group substituted with the above "$C_{3-7}$ cycloalkyl". The "$C_{3-7}$ cycloalkoxy" includes, for example, cyclopropyloxy, cyclobutyloxy, cyclopentyloxy, and cyclohexyloxy, and preferably cyclohexyloxy. The "$C_{5-6}$ cycloalkoxy" means a cycloalkoxy having 5 or 6 carbon atoms within the "$C_{3-7}$ cycloalkoxy".

The "$C_{6-10}$ aryloxy" means oxy group substituted with the above "$C_{6-10}$ aryl". The "$C_{6-10}$ aryloxy" includes, for example, phenyloxy and naphthyloxy, and preferably phenyloxy.

The "5- to 12-membered heteroaryloxy" means oxy group substituted with the above "5- to 12-membered heteroaryl". The "5- to 12-membered heteroaryloxy" includes, for example, pyridyloxy, imidazolyloxy and furyloxy, and preferably pyridyloxy.

The "$C_{1-4}$ alkylamino" means amino group substituted with one or two of the above "$C_{1-4}$ alkyl". The "$C_{1-4}$ alkylamino" includes, for example, methylamino, ethylamino, propylamino, isopropylamino, butylamino, isobutylamino, dimethylamino, diethylamino, and ethylmethylamino, and preferably methylamino and dimethylamino.

The "$C_{3-7}$ cycloalkylamino" means amino group substituted with one or two of the above "$C_{3-7}$ cycloalkyl". The "$C_{3-7}$ cycloalkylamino" includes, for example, cyclopropylamino, cyclobutylamino, cyclopentylamino, cyclohexylamino and dicyclopropylamino, and preferably cyclohexylamino.

The "$C_{1-4}$ alkylsulfonyl" means sulfonyl group substituted with the above "$C_{1-4}$ alkyl". The "$C_{1-4}$ alkylsulfonyl" includes, for example, methylsulfonyl, ethylsulfonyl, propylsulfonyl, isopropylsulfonyl and butylsulfonyl, and preferably methylsulfonyl.

The "$C_{1-4}$ alkylthio" means thio group substituted with the above "$C_{1-4}$ alkyl". The "$C_{1-4}$ alkylthio" includes, for example, methylthio, ethylthio, propylthio, isopropylthio and butylthio, and preferably methylthio.

The "any 1 to 6 hydrogen atoms in the compound of formula (I) may be replaced with deuterium atoms" or the "any 1 to 8 hydrogen atoms in the compound of formula (I') are replaced with deuterium atoms" means that the hydrogen atoms in the compound of formula (I) or (I') are replaced with deuterium atoms, as well as the hydrogen atoms in the above-mentioned $C_{1-6}$ alkyl, $C_{1-6}$ alkoxy, $C_{3-7}$ cycloalkyl, $C_{3-7}$ cycloalkoxy, 3- to 7-membered non-aromatic heterocyclyl, $C_{6-10}$ aryl, $C_{6-10}$ aryloxy, 5- to 12-membered heteroaryl, 5- to 12-membered heteroaryloxy, $C_{1-4}$ alkylthio, or $C_{1-4}$ alkylsulfonyl are replaced with deuterium atoms. For example, it includes ($^2H_3$) methyl, ($^2H_5$) ethyl, ($^2H_3$) methoxy, ($^2H_5$)phenyl, ($^2H_5$) phenoxy, etc.

In order to disclose the present compound of the above formula (I) or (I') in more detail, each symbol used in the formula (I) or (I') is further explained below showing preferred examples.

In an embodiment, $R^{1a}$, $R^{1b}$, $R^{1c}$, and $R^{1d}$ are independently, hydrogen, deuterium, halogen, cyano, $C_{1-4}$ alkyl, $C_{1-4}$ alkoxy, $C_{1-4}$ alkylamino (wherein the alkyl and the alkyl moiety in the alkoxy and the alkylamino may be independently substituted with 1 to 3 substituents selected independently from the group consisting of deuterium, halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), $C_{3-7}$ cycloalkyl, $C_{3-7}$ cycloalkoxy, $C_{3-7}$ cycloalkylamino (wherein the cycloalkyl and the cycloalkyl moiety in the cycloalkoxy and the cycloalkylamino may be independently substituted with 1 to 3 substituents selected independently from the group consisting of deuterium, halogen, hydroxy group, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), $C_{6-10}$ aryl, $C_{6-10}$ aryloxy, 5- to 12-membered heteroaryl, or 5- to 12-membered heteroaryloxy (wherein the aryl and the aryl moiety in the aryloxy, and the heteroaryl and the heteroaryl moiety in the heteroaryloxy may be independently substituted with 1 to 3 substituents selected independently from the group consisting of deuterium, halogen, cyano, $C_{1-4}$ alkyl optionally-substituted with 1 to 3 substituents selected independently from Substituent-group A and deuterium, $C_{1-4}$ alkoxy optionally-substituted with 1 to 3 substituents selected independently from Substituent-group A and deuterium, $C_{3-7}$ cycloalkyl optionally-substituted with 1 to 3 substituents selected independently from Substituent-group B and deuterium, $C_{3-7}$ cycloalkoxy optionally-substituted with 1 to 3 substituents selected independently from Substituent-group B and deuterium, 3- to 7-membered non-aromatic heterocyclyl optionally-substituted with 1 to 3 substituents selected independently from Substituent-group B and deuterium, $C_{1-4}$ alkylthio optionally-substituted with 1 to 3 substituents selected independently from Substituent-group A and deuterium, and $C_{1-4}$ alkylsulfonyl optionally-substituted with 1 to 3 substituents selected independently from Substituent-group A and deuterium). Provided that at least one of $R^{1a}$, $R^{1b}$, $R^{1c}$ and $R^{1d}$ is the above-mentioned $C_{6-10}$ aryl, $C_{6-10}$ aryloxy, 5- to 12-membered heteroaryl, or 5- to 12-membered heteroaryloxy.

In another embodiment, $R^{1a}$, $R^{1b}$, $R^{1c}$, and $R^{1d}$ are independently, hydrogen, halogen, cyano, $C_{1-4}$ alkyl, $C_{1-4}$ alkoxy (wherein the alkyl and the alkyl moiety in the alkoxy may be independently substituted with 1 to 3 the same or different halogen atoms), $C_{6-10}$ aryl, $C_{6-10}$ aryloxy, 5- to 12-membered heteroaryl, or 5- to 12-membered heteroaryloxy (wherein the aryl and the aryl moiety in the aryloxy, and the heteroaryl and the heteroaryl moiety in the heteroaryloxy may be independently substituted with 1 to 3 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, and $C_{1-4}$ alkylsulfonyl optionally-substituted with 1 to 3 substituents selected independently from Substituent-group A). Provided that at least one of $R^{1a}$, $R^{1b}$, $R^{1c}$ and Rid is the above-mentioned $C_{6-10}$ aryl, $C_{6-10}$ aryloxy, 5- to 12-membered heteroaryl, or 5- to 12-membered heteroaryloxy.

In another embodiment of $R^{1a}$, $R^{1b}$, $R^{1c}$, and $R^{1d}$, $R^{1a}$ and $R^{1d}$ are hydrogen; and $R^{1b}$ and $R^{1c}$ are independently hydrogen, $C_{6-10}$ aryl, $C_{6-10}$ aryloxy, 5- to 12-membered heteroaryl, or 5- to 12-membered heteroaryloxy (wherein the aryl and the aryl moiety in the aryloxy, and the heteroaryl and the heteroaryl moiety in the heteroaryloxy may be independently substituted with 1 to 3 substituents selected independently from the group consisting of halogen, $C_{1-4}$ alkyl optionally-substituted with 1 to 3 substituents selected independently from Substituent-group A, and $C_{1-4}$ alkoxy optionally-substituted with 1 to 3 substituents selected independently from Substituent-group A). Provided that both of $R^{1b}$ and $R^{1c}$ are not hydrogen.

In another embodiment of $R^{1a}$, $R^{1b}$, $R^{1c}$, and $R^{1d}$, $R^{1a}$ and $R^{1d}$ are hydrogen; and either one of $R^{1b}$ and $R^{1c}$ is $C_{6-10}$ aryl, $C_{6-10}$ aryloxy, 5- to 12-membered heteroaryl, or 5- to 12-membered heteroaryloxy (wherein the aryl and the aryl moiety in the aryloxy, and the heteroaryl and the heteroaryl moiety in the heteroaryloxy may be independently substituted with 1 to 3 substituents selected independently from the group consisting of halogen, $C_{1-4}$ alkyl optionally-substituted with 1 to 3 substituents selected independently from Substituent-group A, and $C_{1-4}$ alkoxy optionally-substituted with 1 to 3 substituents selected independently from Substituent-group A), and the other one is hydrogen.

In another embodiment of $R^{1a}$, $R^{1b}$, $R^{1c}$, and $R^{1d}$, $R^{1a}$, $R^{1c}$ and $R^{1d}$ are hydrogen, and $R^{1b}$ is $C_{6-10}$ aryl, $C_{6-10}$ aryloxy, 5- to 12-membered heteroaryl, or 5- to 12-membered heteroaryloxy (wherein the aryl and the aryl moiety in the aryloxy, and the heteroaryl and the heteroaryl moiety in the heteroaryloxy may be independently substituted with 1 to 3 substituents selected independently from the group consisting of halogen, $C_{1-4}$ alkyl optionally-substituted with 1 to 3 substituents selected independently from Substituent-group A, and $C_{1-4}$ alkoxy optionally-substituted with 1 to 3 substituents selected independently from Substituent-group A).

Preferred examples of $R^{1a}$, $R^{1b}$, $R^{1c}$, and Rid include hydrogen, deuterium, fluorine, chlorine, methyl, ($^2H_3$)methyl, ethyl, ($^2H_5$)ethyl, isopropyl, isobutyl, cyclopropyl, cyclopentyl, cyclohexyl, methoxy, ($^2H_3$)methoxy, ethoxy, phenyl, ($^2H_5$)phenyl, 2-fluorophenyl, 3-fluorophenyl, 4-fluorophenyl, 4-(trifluoromethyl)phenyl, 4-(trifluoromethyl)-(2,3,5,6-$^2H_4$)phenyl, 5-(trifluoromethyl)pyridin-2-yl, phenoxy, ($^2H_5$)phenoxy, 3-fluorophenoxy, 4-fluorophenoxy, 3,4-difluorophenoxy, 3,5-difluorophenoxy, 4-chlorophenoxy, 4-methylphenoxy, 4-(trifluoromethyl)phenoxy, 4-methoxyphenoxy, 4-(trifluoromethoxy)phenoxy, 4-cyanophenoxy, 4-(methylsulfonyl)phenoxy, (5-methylpyridin-2-yl)oxy, (5-(trifluoromethyl)pyridin-2-yl)oxy, (5-fluoropyridin-2-yl)oxy, 2-methoxy-4-(trifluoromethyl)phenyl, 2-fluoro-4-(trifluoromethyl)phenyl, 2-chloro-4-(trifluoromethyl)phenyl, 4-(trifluoromethoxy)phenyl, (5-chloropyridin-2-yl)oxy, 2,4-dichlorophenyl, 2-chloro-4-fluorophenoxy, 4-chloro-2-fluorophenoxy, and 2,4-dichlorophenoxy.

More preferred examples of $R^{1a}$, $R^{1b}$, $R^{1c}$, and $R^{1d}$ include hydrogen, fluorine, 4-(trifluoromethyl)phenyl, 5-(trifluoromethyl)pyridin-2-yl, 3-fluorophenoxy, 4-fluorophenoxy, 4-chlorophenoxy, 4-methylphenoxy, 4-(trifluoromethyl)phenoxy, 4-(trifluoromethoxy)phenoxy, (5-methylpyridin-2-yl)oxy, (5-(trifluoromethyl)pyridin-2-yl)oxy, 2-methoxy-4-(trifluoromethyl)phenyl, 4-(trifluoromethoxy)phenyl, and (5-chloropyridin-2-yl)oxy.

Even more preferred examples of $R^{1a}$, $R^{1b}$, $R^{1c}$, and Rid include hydrogen, 4-(trifluoromethyl)phenyl, 5-(trifluoromethyl)pyridin-2-yl, 4-fluorophenoxy, 4-chlorophenoxy, 4-(trifluoromethyl)phenoxy, 4-(trifluoromethoxy)phenoxy, (5-(trifluoromethyl)pyridin-2-yl)oxy, 2-methoxy-4-(trifluoromethyl)phenyl, 4-(trifluoromethoxy)phenyl, and (5-chloropyridin-2-yl)oxy.

As preferred combination of $R^{1a}$, $R^{1b}$, $R^{1c}$, and $R^{1d}$; $R^{1a}$, $R^{1c}$ and $R^{1d}$ are hydrogen; $R^{1b}$ is 4-(trifluoromethyl)phenyl, 5-(trifluoromethyl)pyridin-2-yl, 4-fluorophenoxy, 4-chlorophenoxy, 4-(trifluoromethyl)phenoxy, 4-(trifluoromethoxy)phenoxy, (5-(trifluoromethyl)pyridin-2-yl)oxy, 2-methoxy-4-(trifluoromethyl)phenyl, 4-(trifluoromethoxy)phenyl, or (5-chloropyridin-2-yl)oxy.

Preferably, $R^2$ and $R^3$ are independently hydrogen, deuterium, or $C_{1-6}$ alkyl which may be independently substituted with 1 to 5 substituents selected independently from the group consisting of deuterium, cyano, halogen, hydroxy group, and $C_{1-4}$ alkoxy optionally-substituted with 1 to 3 substituents selected independently from Substituent-group A; preferably hydrogen or $C_{1-6}$ alkyl optionally-substituted with 1 to 5 halogen atoms.

Preferably, $R^2$ and $R^3$ are, for example, hydrogen, deuterium, methyl, ($^2H_3$)methyl, ethyl, ($^2H_5$)ethyl, isopropyl, isobutyl, trifluoromethyl, cyclopropyl, cyclopentyl, and cyclohexyl; more preferably hydrogen, methyl, and ethyl.

Additionally, in another preferred embodiment, $R^2$ and $R^3$ includes the following group of formula (II) with —$OR^4$, which is formed by combining together $R^2$ and $R^3$ with the carbon atom to which they are attached to form a ring.

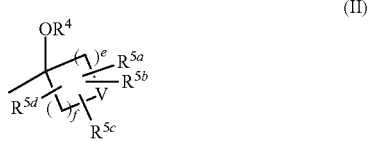

(II)

In the above formula (II),
preferably, e and f are independently 1 or 2,
preferably, V is single bond or oxygen atom.
Preferably, $R^{5a}$, $R^{5b}$, $R^{5c}$, and $R^{5d}$ are independently hydrogen or halogen.

Preferably, $R^4$ includes hydrogen, deuterium, $C_{1-4}$ alkyl (which may be substituted with 1 to 3 substituents selected independently from the group consisting of the same or different halogen atoms and deuterium), and $C_{3-7}$ cycloalkyl (which may be independently substituted with 1 to 3 substituents selected independently from the group consisting of deuterium, halogen, hydroxy group, and $C_{1-4}$ alkoxy optionally-substituted with 1 to 3 substituents selected independently from Substituent-group A); more preferably hydrogen.

Preferably, $R^4$ includes, for example, hydrogen, deuterium, methyl, ($^2H_3$)methyl, ethyl, ($^2H_5$)ethyl, propyl, isopropyl, cyclopropyl, cyclobutyl, cyclopentyl, and cyclohexyl; more preferably hydrogen, isopropyl, and cyclopentyl; even more preferably hydrogen.

Preferably, m is 0 or 1, more preferably 0.
L is $CR^7R^8$, provided that when m is 2, each $CR^7R^8$ is independently the same or different.

Preferably, $R^7$ and $R^8$ include independently hydrogen, deuterium, and $C_{1-4}$ alkyl which may be independently substituted with 1 to 3 substituents selected independently from the group consisting of deuterium, halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B; more preferably hydrogen.

Preferably, $R^7$ and $R^8$ include, for example, hydrogen, deuterium, methyl, ($^2H_3$)methyl, ethyl, and ($^2H_5$)ethyl; more preferably hydrogen.

Preferably, Substituent-group A includes deuterium, fluorine, chlorine, hydroxy group, $C_{1-2}$ alkoxy, and $C_{5-6}$ cycloalkoxy; more preferably fluorine, hydroxy group, and $C_{1-2}$ alkoxy.

Preferably, Substituent-group B includes deuterium, fluorine, chlorine, hydroxy group, $C_{1-2}$ alkyl, $C_{1-2}$ alkoxy, and $C_{5-6}$ cycloalkoxy; more preferably fluorine, hydroxy group, $C_{1-2}$ alkyl, and $C_{1-2}$ alkoxy.

As preferred combination of two E in formula (I'), both or either is deuterium; more preferably both are deuterium.

One embodiment of the compound of formula (I) or (I') includes the following:
the compound or a pharmaceutically acceptable salt thereof wherein
$R^{1a}$, $R^{1b}$, $R^{1c}$, and $R^{1d}$ are independently hydrogen, deuterium, $C_{6-10}$ aryl, $C_{6-10}$ aryloxy, 5- to 12-membered heteroaryl, or 5- to 12-membered heteroaryloxy, wherein the aryl and the aryl moiety in the aryloxy, and the heteroaryl and the heteroaryl moiety in the heteroaryloxy may be independently substituted with 1 to 3 substituents selected independently from the group consisting of deuterium, halogen, $C_{1-4}$ alkyl optionally-substituted with 1 to 3 substituents selected independently from Substituent-group A and deuterium, and $C_{1-4}$ alkoxy optionally-substituted with 1 to 3 substituents selected independently from Substituent-group A and deuterium, provided that at least one of $R^{1a}$, $R^{1b}$, $R^{1c}$ and $R^{1d}$ is the above $C_{6-10}$ aryl, $C_{6-10}$ aryloxy, 5- to 12-membered heteroaryl or 5- to 12-membered heteroaryloxy,
$R^2$ and $R^3$ are independently hydrogen, deuterium, or $C_{1-6}$ alkyl which may be independently substituted with 1 to 5 substituents selected independently from the group consisting of deuterium, cyano, halogen, hydroxy group, and $C_{1-4}$ alkoxy optionally-substituted with 1 to 3 substituents selected independently from Substituent-group A, provided that both of $R^2$ and $R^3$ are not hydrogen, or
$R^2$ and $R^3$ may be combined together with the carbon atom to which they are attached to form a ring, i.e., the following group of formula (IIa) with —$OR^4$

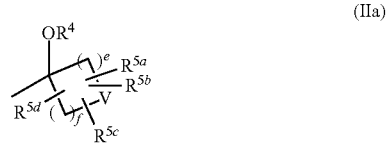

(IIa)

in formula (IIa),
e and f are independently 1 or 2,
$R^4$ is hydrogen, deuterium, $C_{1-6}$ alkyl (which may be substituted with 1 to 3 substituents selected independently from the group consisting of deuterium, halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), or $C_{3-7}$ cycloalkyl (which may be independently substituted with 1 to 3 substituents selected independently from the group consisting of deuterium, halogen, hydroxy group, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), V is single bond or oxygen atom, and $R^{5a}$, $R^{5b}$, $R^{5c}$, and $R^{5d}$ are independently hydrogen, deuterium or halogen, $R^4$ is hydrogen, deuterium, $C_{1-4}$ alkyl (which may be substituted with 1 to 3 substituents selected independently from the group consisting of halogen and deuterium), or $C_{3-7}$ cycloalkyl (which may be substituted with 1 to 3 substituents selected independently from the group consisting of deuterium, halogen, hydroxy group, and $C_{1-4}$ alkoxy optionally-substituted with 1 to 3 substituents selected independently from Substituent-group A), m is 0 or 1, L is $CR^7R^8$, $R^7$ and $R^8$ are independently hydrogen, deuterium, or $C_{1-4}$ alkyl which may be independently substituted with 1 to 3 substituents selected independently from the group consisting of deuterium, halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, further, as for the compound of formula (I'), both or either of E is deuterium.

Another embodiment of the compound of formula (I) or (I') includes the following:

the compound or a pharmaceutically acceptable salt thereof wherein $R^{1a}$ and $R^{1d}$ are hydrogen, at least one of $R^{1b}$ and $R^{1c}$ is $C_{6-10}$ aryl, $C_{6-10}$ aryloxy, 5- to 12-membered heteroaryl, or 5- to 12-membered heteroaryloxy, wherein the aryl and the aryl moiety in the aryloxy, and the heteroaryl and the heteroaryl moiety in the heteroaryloxy may be independently substituted with 1 to 3 substituents selected independently from the group consisting of halogen, $C_{1-4}$ alkyl optionally-substituted with 1 to 3 substituents selected independently from Substituent-group A, and $C_{1-4}$ alkoxy optionally-substituted with 1 to 3 substituents selected independently from Substituent-group A, $R^2$ and $R^3$ are independently $C_{1-6}$ alkyl optionally-substituted with 1 to 5 the same or different halogen atoms, or $R^2$ and $R^3$ may be combined together with the carbon atom to which they are attached to form a ring, i.e., the following group of formula (IIb) with —$OR^4$

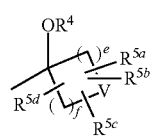

(IIb)

in formula (IIb),
e and f are 1,
$R^4$ is hydrogen,
V is oxygen atom, $R^{5a}$, $R^{5b}$, $R^{5c}$, and $R^{5d}$ are independently hydrogen or halogen, $R^4$ is hydrogen, m is 0 or 1, L is $CR^7R^8$, $R^7$ and $R^8$ are independently hydrogen or $C_{1-4}$ alkyl which may be substituted with 1 to 3 the same or different halogen atoms, further, as for the compound of formula (I), any 1 to 6 hydrogen atoms are replaced with deuterium, as for the compound of formula (I'), any 1 to 8 hydrogen atoms are replaced with deuterium.

Another embodiment of the compound of formula (I) or (I') includes the following:

the compound or a pharmaceutically acceptable salt thereof wherein $R^{1a}$ and $R^{1d}$ are hydrogen, either one of $R^{1b}$ and $R^{1c}$ is phenyl, 2-fluorophenyl, 3-fluorophenyl, 4-fluorophenyl, 4-(trifluoromethyl)phenyl, 5-(trifluoromethyl)pyridin-2-yl, phenoxy, 3-fluorophenoxy, 3,4-difluorophenoxy, 3,5-difluorophenoxy, 4-chlorophenoxy, 4-(trifluoromethyl)phenoxy, 4-(trifluoromethoxy)phenoxy, 4-cyanophenoxy, 4-(methylsulfonyl)phenoxy, (5-methylpyridin-2-yl)oxy, (5-(trifluoromethyl)pyridin-2-yl)oxy, (5-fluoropyridin-2-yl)oxy, 2-methoxy-4-(trifluoromethyl)phenyl, 2-fluoro-4-(trifluoromethyl)phenyl, 2-chloro-4-(trifluoromethyl)phenyl, 4-(trifluoromethoxy)phenyl, (5-chloropyridin-2-yl)oxy, 2,4-dichlorophenyl, 2-chloro-4-fluorophenoxy, 4-chloro-2-fluorophenoxy, or 2,4-dichlorophenoxy, and the other one is hydrogen, both of $R^2$ and $R^3$ are methyl, or $R^2$ and $R^3$ are combined together with the carbon atom to which they are attached to form the following group of formula (IIc) with —$OR^4$

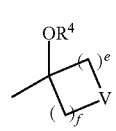

(IIc)

in formula (IIc), e and f are 1, $R^4$ is hydrogen, V is single bond or oxygen atom, m is 0, further, as for the compound of formula (I'), E is deuterium.

Processes to prepare the compounds of the present invention are mentioned below. The compound (I) or (I') of the present invention can be prepared, for example, according to Processes 1 to 5 shown below. In the following processes, any hydrogen atoms besides E in each compound may be optionally replaced with deuterium, if possible.

Process 1:

The compound of formula (I) or (I') wherein $R^{1b}$ is $OR^a$, i.e., Compound (S-5) or a pharmaceutically acceptable salt thereof can be prepared, for example, according to the following process.

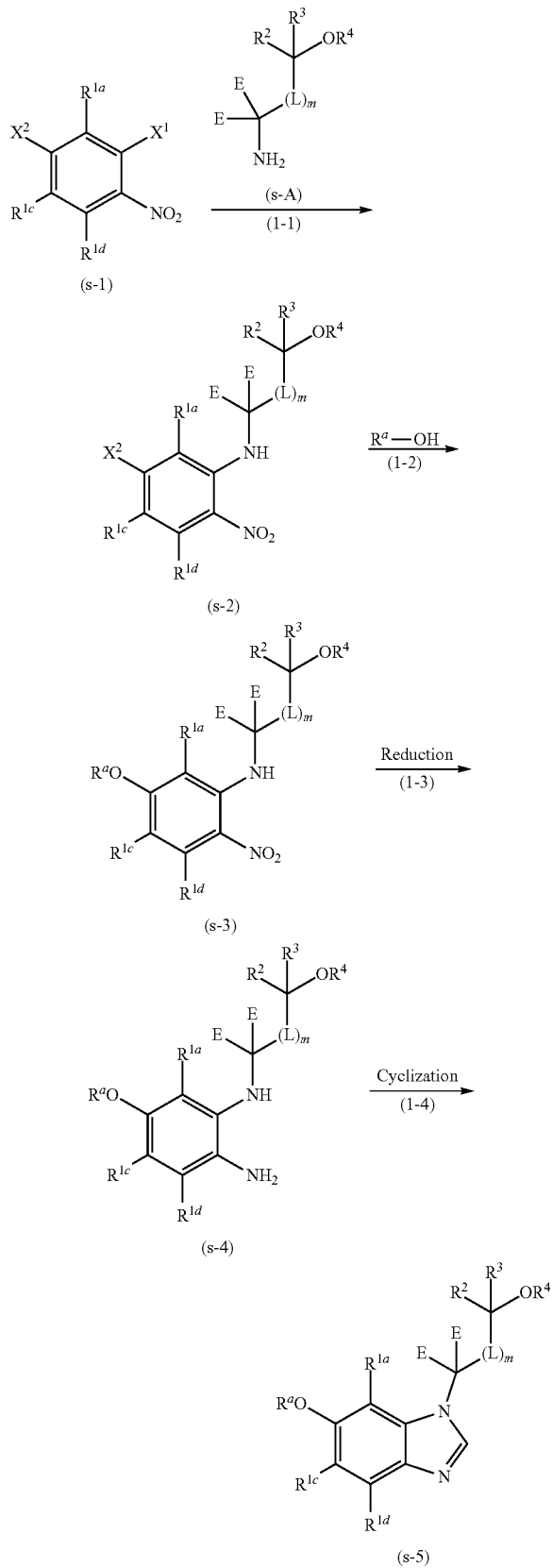

In the above scheme, E is the same or different and hydrogen or deuterium; $R^{1a}$, $R^{1c}$, Rid, $R^2$, $R^3$, $R^4$, L, and m are as defined in Item 1; $R^aO$— means $R^{1b}$ which is selected from $C_{1-4}$ alkoxy optionally-substituted with 1 to 3 substituents selected independently from Substituent-group A, $C_{3-7}$ cycloalkoxy optionally-substituted with 1 to 3 substituents selected independently from Substituent-group B, $C_{6-10}$ aryloxy optionally-substituted with 1 to 3 substituents selected independently from Substituent-group B, or 5- to 12-membered heteroaryloxy optionally-substituted with 1 to 3 substituents selected independently from Substituent-group B; and $X^1$ and $X^2$ are independently a leaving group such as halogen, trifluoromethanesulfonyloxy, and methanesulfonyloxy.

Step (1-1):

This step is a process to prepare nitroaniline compound (s-2) by reacting nitrobenzene compound (s-1) and amine compound (s-A). The base used herein includes an inorganic base such as sodium hydroxide, potassium hydroxide, potassium carbonate, and cesium carbonate, and an organic base such as triethylamine and diisopropylethylamine. When the amine compound is used in large excess, it is not necessary to use such base. The solvent used herein includes ethers such as THF, 1,2-dimethoxyethane, and 1,4-dioxane; DMF; NMP; acetonitrile; and the like. The reaction time is generally about 10 minutes to about 10 hours, and the reaction temperature is 0° C. to boiling point of a solvent used herein.

Step (1-2):

This step is a process to prepare nitroaniline compound (s-3) by reacting compound (s-2) and a compound having hydroxy group. The base used herein includes sodium hydroxide, potassium hydroxide, potassium carbonate, cesium carbonate, sodium hydride, and the like. The solvent used herein includes ethers such as THF, 1,2-dimethoxyethane, and 1,4-dioxane; DMF; NMP; and acetonitrile. The reaction time is generally about 10 minutes to about 10 hours, and the reaction temperature is 0° C. to boiling point of a solvent used herein.

Step (1-3):

This step is a process to prepare phenylenediamine compound (s-4) by reducing compound (s-3). The reaction condition in this step includes generally-used conditions for reducing a nitro group, for example, catalytic reduction under hydrogenation condition with palladium-carbon, etc.; metal reduction with zinc, iron, etc.; and hydride reduction with lithium aluminum hydride, etc. The solvent used in this reduction includes various solvents generally-used in each reduction condition. In case of catalytic reduction, it includes methanol, ethanol, THF, and ethyl acetate; in case of metal reduction, it includes THF, acetic acid, methanol, and ethanol; and in case of hydride reduction, it includes diethyl ether, and THF. The reaction time is generally 10 minutes to 24 hours, and the reaction temperature is 0° C. to boiling point of a solvent used herein.

Step (1-4):

This step is a process to prepare Compound (S-5) by reacting compound (s-4) and formic acid or a formic acid equivalent to be cyclized. The formic acid equivalent includes orthoformates such as methyl orthoformate and ethyl orthoformate. In the present step, a catalyst may be used, which includes an organic acid such as formic acid and acetic acid, and Lewis acid such as ytterbium triflate. The solvent used herein includes alcohols such as methanol and ethanol. It is also possible to use formic acid, orthoformate and the like as a solvent, which are mentioned above as a reactant. The reaction time is generally 10 minutes to 24 hours, and the reaction temperature is room temperature to boiling point of a solvent used herein.

Step (1-1) and Step (1-2) may be sequentially performed; for example, to the mixture after the reaction of Step (1-1) is completed, the reagents to be used in Step (1-2) can be added to prepare compound (s-3) to which two substituents are introduced in one step. The reaction time of the sequential reactions is generally 20 minutes to 20 hours.

Process 2:

The nitroaniline compound of formula (s-3) can be also prepared, for example, according to the following process.

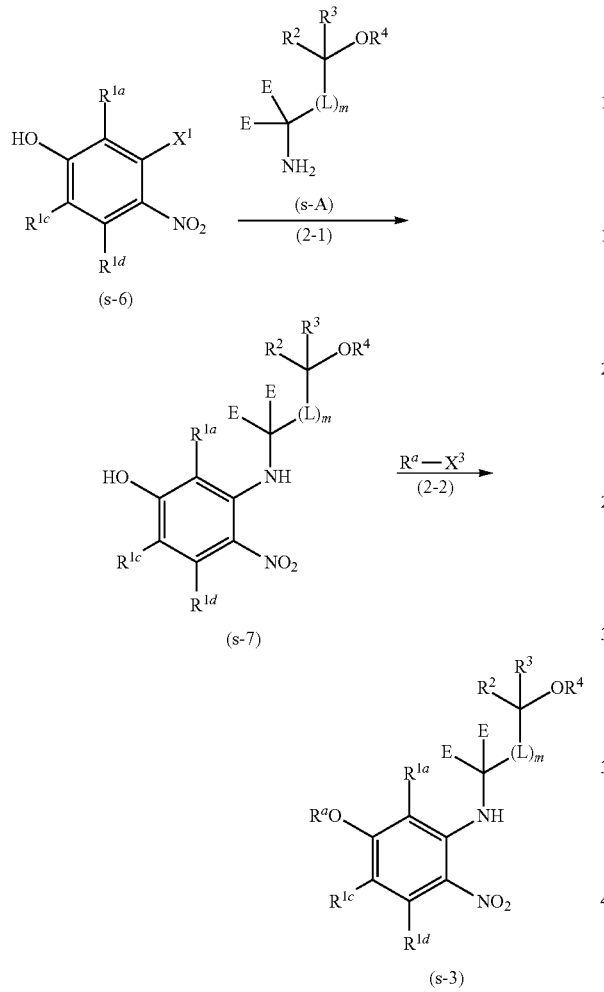

includes ethers such as THF, 1,2-dimethoxyethane, and 1,4-dioxane; DMF; NMP; acetonitrile; and the like. The reaction time is generally about 10 minutes to about 10 hours, and the reaction temperature is 0° C. to boiling point of a solvent used herein.

Step (2-1) and Step (2-2) may be sequentially performed; for example, to the mixture after the reaction of Step (2-1) is completed, the reagents to be used in Step (2-2) can be added to prepare compound (s-3) to which two substituents are introduced in one step. The reaction time of the sequential reactions is generally 20 minutes to 20 hours.

Process 3:

The compound of formula (I) or (I') wherein $R^{1b}$ is $OR^a$, i.e., Compound (S-5) or a pharmaceutically acceptable salt thereof can be also prepared, for example, according to the following process.

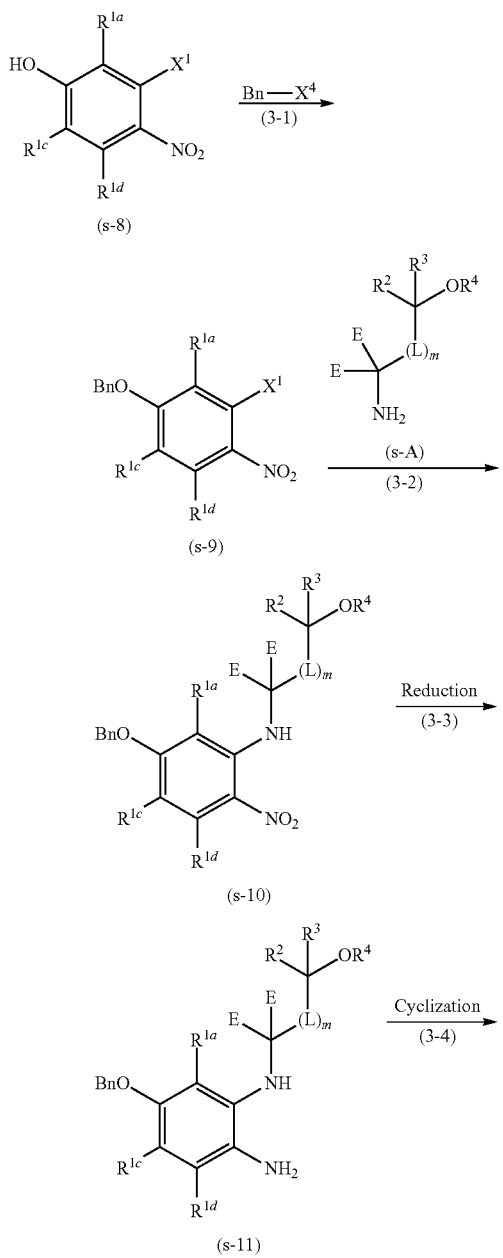

In the above scheme, E is the same or different and hydrogen or deuterium; $R^{1a}$, $R^{1c}$, $R^{1d}$, $R^2$, $R^3$, $R^4$, L, and m are as defined in Item 1; $R^aO$— means $R^{1b}$ which is selected from $C_{1-4}$ alkoxy optionally-substituted with 1 to 3 substituents selected independently from Substituent-group A, $C_{3-7}$ cycloalkoxy optionally-substituted with 1 to 3 substituents selected independently from Substituent-group B, $C_{6-10}$ aryloxy optionally-substituted with 1 to 3 substituents selected independently from Substituent-group B, or 5- to 12-membered heteroaryloxy optionally-substituted with 1 to 3 substituents selected independently from Substituent-group B; and $X^1$ and $X^3$ are independently a leaving group such as halogen, trifluoromethanesulfonyloxy, and methanesulfonyloxy.

Step (2-1):

This step is a process to prepare an aminophenol compound of formula (s-7) from a phenol compound of formula (s-6) in the same manner as Step (1-1).

Step (2-2):

This step is a process to prepare a nitroaniline compound of formula (s-3) by reacting a compound of formula (s-7) with $R^a$—$X^3$. The base used herein includes sodium hydroxide, potassium hydroxide, potassium carbonate, cesium carbonate, and sodium hydride. The solvent used herein

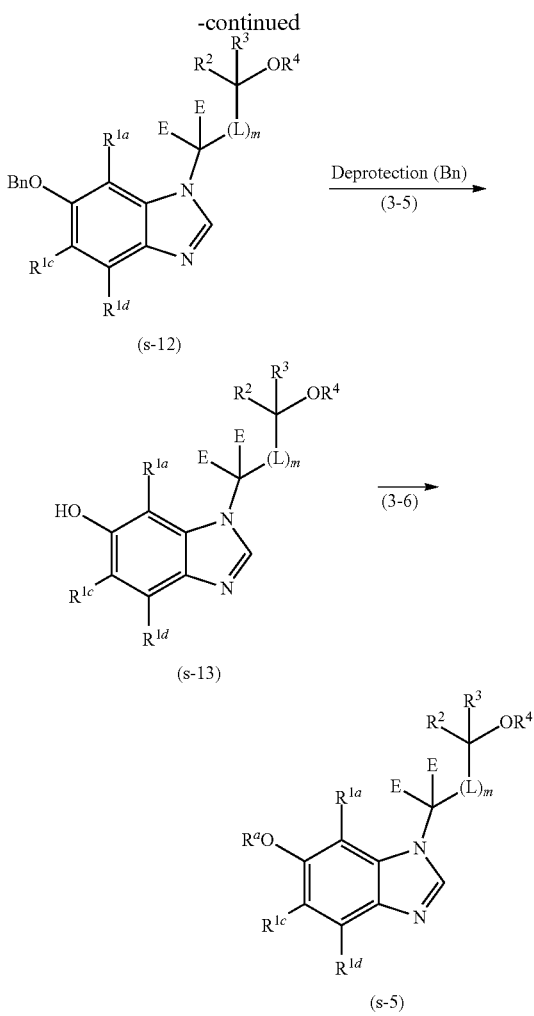

In the above scheme, E is the same or different and hydrogen or deuterium; $R^{1a}$, $R^{1c}$, $R^{1d}$, $R^2$, $R^3$, $R^4$, L, and m are as defined in Item 1; $R^a$ is as defined above; $X^1$ and $X^4$ are independently a leaving group such as halogen, trifluoromethanesulfonyloxy, and methanesulfonyloxy. Bn means benzyl group, which may encompass a protecting group that can be deprotected like benzyl group, for example, substituted benzyl group disclosed in Protective Groups in Organic Synthesis.

Step (3-1):
This step is a process to prepare an ether compound of formula (s-9) by reacting a phenol compound of formula (s-8) with Bn-$X^4$, for example, in the presence of a base. The base used herein includes sodium carbonate, potassium carbonate, cesium carbonate, and sodium hydride. Bn-$X^4$ includes benzyl chloride and benzyl bromide. As appropriate, sodium iodide, potassium iodide, tetrabutylammonium iodide, tetrabutylammonium hydrogen sulfate, etc. may be added to the reaction. The solvent used herein includes acetone, acetonitrile, THF, diethyl ether, 1,4-dioxane, 1,2-dimethoxyethane, DMF, and NMP. The reaction time is generally 30 minutes to 24 hours, and the reaction temperature is 0° C. to boiling point of a solvent used herein. In addition, a compound of formula (s-9) can be prepared from a compound of formula (s-8) according to the method (condition) described in Protective Groups in Organic Synthesis or the like.

Step (3-2):
This step is a process to prepare a nitroaniline compound of formula (s-10) from a compound of formula (s-9) in the same manner as Step (1-1).

Step (3-3):
This step is a process to prepare a phenylenediamine compound of formula (s-11) by selectively reducing the nitro group in a compound of formula (s-10). The reaction condition in this step includes catalytic reduction with sulfur-poisoning platinum-carbon, etc. under hydrogenation condition; metal reduction with zinc, iron, tin, etc.; hydride reduction with lithium aluminum hydride, etc. The solvent used in this reduction includes various solvents generally-used in each reduction condition. In case of catalytic reduction, it includes methanol, ethanol, THF, and ethyl acetate; in case of metal reduction, it includes THF, acetic acid, methanol, and ethanol; and in case of hydride reduction, it includes diethyl ether, and THF. The reaction time is generally 10 minutes to 24 hours, and the reaction temperature is 0° C. to boiling point of a solvent used herein.

Step (3-4):
This step is a process to prepare a benzimidazole compound of formula (s-12) from a compound of formula (s-11) in the same manner as Step (1-4).

Step (3-5):
This step is a process to prepare a hydroxybenzimidazole compound of formula (s-13) by deprotecting the protecting group of hydroxy group in a compound of formula (s-12), for example, by catalytic reduction under hydrogenation condition. The catalyst used herein includes heterogenous catalysts such as palladium-carbon. The hydrogenation condition means "under hydrogen atmosphere", or "in the presence of formic acid, ammonium formate, etc." The solvent used herein includes methanol, ethanol, THF, and ethyl acetate. The reaction time is generally 30 minutes to 24 hours, and the reaction temperature is 0° C. to boiling point of a solvent used herein. In addition, a compound of formula (s-13) can be prepared from a compound of formula (s-12) in the method (condition) described in Protective Groups in Organic Synthesis, etc.

Step (3-6):
This step is a process to prepare a compound of formula (S-5) from a compound of formula (s-13), which includes two reaction conditions, but should not be limited thereto.

1) A reaction condition herein using a base includes the following step: a compound of formula (S-5) is prepared by reacting a compound of formula (s-13) and $R^a$—$X^5$ (wherein $R^a$ is $C_{1-4}$ alkyl optionally-substituted with 1 to 3 substituents selected independently from Substituent-group A, $C_{3-7}$ cycloalkyl optionally-substituted with 1 to 3 substituents selected independently from Substituent-group B, $C_{6-10}$ aryl optionally-substituted with 1 to 3 substituents selected independently from Substituent-group B, or 5- to 12-membered heteroaryl optionally-substituted with 1 to 3 substituents selected independently from Substituent-group B, which are defined in $R^{1b}$, and $X^5$ is as defined in the above $X^1$) in the same manner as Step (2-2).

2) A reaction condition herein using a catalyst and a base includes a reaction with a boronate compound or a halogen compound which has $R^a$ group. The catalyst used herein includes copper(II) acetate, copper(I) iodide, and copper(II) oxide. The base used herein includes potassium carbonate, cesium carbonate, potassium hydroxide, and triethylamine. The solvent used herein includes chloroform, 1,4-dioxane, DMF, DMSO, and NMP. The reaction time is generally 30 minutes to 24 hours, and the reaction temperature is room temperature to boiling point of a solvent used herein.

A compound of formula (I) or (I') wherein any one or more of $R^{1a}$, $R^{1b}$, $R^{1c}$, and $R^{1d}$ are $OR^a$ or a pharmaceutically acceptable salt thereof can be also prepared in the same manner as above.

Process 4:

The compound of formula (I) or (I') wherein $R^{1b}$ is $R^b$ (aryl or heteroaryl), i.e., Compound (S-16) or a pharmaceutically acceptable salt thereof can be prepared, for example, according to the following process.

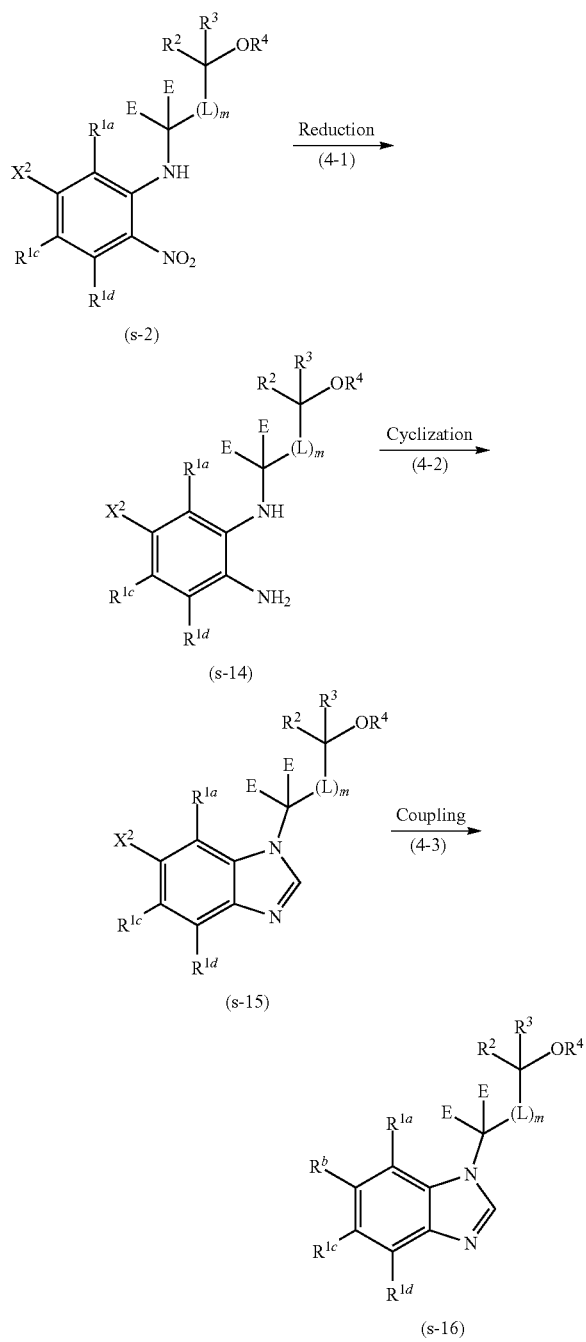

In the above scheme, E is the same or different and hydrogen or deuterium; $R^{1a}$, $R^{1c}$, $R^{1d}$, $R^2$, $R^3$, $R^4$, L, and m are as defined in Item 1; $X^2$ is as defined above; and $R^b$ is $C_{6-10}$ aryl or 5- to 12-membered heteroaryl, wherein the aryl and the heteroaryl may be independently substituted with 1 to 5 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, 3- to 7-membered non-aromatic heterocyclyl optionally-substituted with 1 to 3 substituents selected independently from Substituent-group B, $C_{1-4}$ alkylthio optionally-substituted with 1 to 3 substituents selected independently from Substituent-group A, and $C_{1-4}$ alkylsulfonyl optionally-substituted with 1 to 3 substituents selected independently from Substituent-group A.

Step (4-1):

This step is a process to prepare a phenylenediamine compound of formula (s-14) by selectively reducing the nitro group in a nitroaniline compound of formula (s-2). The reaction condition in this step includes catalytic reduction with sulfur-poisoning platinum-carbon, etc. under hydrogenation condition; metal reduction with zinc, iron, tin, etc.; hydride reduction with lithium aluminum hydride, etc. The solvent used in this reduction includes various solvents generally-used in each reduction condition. In case of catalytic reduction, it includes methanol, ethanol, THF, and ethyl acetate; in case of metal reduction, it includes THF, acetic acid, methanol, and ethanol; and in case of hydride reduction, it includes diethyl ether, and THF. The reaction time is generally 10 minutes to 24 hours, and the reaction temperature is 0° C. to boiling point of a solvent used herein.

Step (4-2):

This step is a process to prepare a benzimidazole compound of formula (s-15) from a compound of formula (s-14) in the same manner as Step (1-4)

Step (4-3):

This step is a process to prepare a compound of formula (S-16) by reacting a compound of formula (s-15) and boronic acid or boronate compound which has $R^b$ group in the presence of a base and a catalyst. For example, this step is Suzuki coupling reaction. The base used herein includes sodium carbonate, potassium carbonate, cesium carbonate, and tripotassium phosphate. The catalyst used herein includes palladium acetate, tetrakis(triphenylphosphine)palladium, and tris(dibenzylideneacetone)dipalladium. The solvent used herein includes 1,4-dioxane, toluene, and 1,2-dimethoxyethane. The reaction time is generally 30 minutes to 24 hours, and the reaction temperature is room temperature to boiling point of a solvent used herein.

A compound of formula (I) wherein any one or more of $R^{1a}$, $R^{1b}$, $R^{1c}$, and $R^{1d}$ are $R^b$ or a pharmaceutically acceptable salt thereof can be also prepared in the same manner as above.

Process 5:

The compound of formula (I) or (I') wherein $R^{1b}$ is $R^b$, i.e., Compound (S-16) or a pharmaceutically acceptable salt thereof can be also prepared, for example, according to the following process.

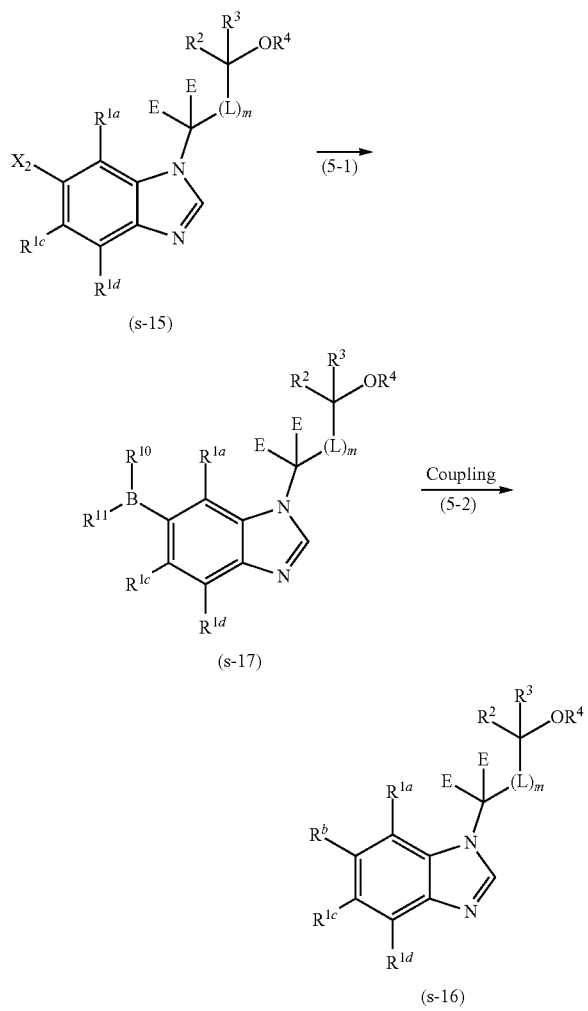

(s-15)

(s-17)

(s-16)

In the above scheme, E is the same or different and hydrogen or deuterium; $R^{1a}$, $R^{1c}$, $R^{1d}$, $R^2$, $R^3$, $R^4$, L, and m are as defined in Item 1; $R^b$ and $X^2$ are as defined above; and $R^{10}$ and $R^{11}$ are independently optionally-substituted $C_{1-4}$ alkyl, optionally-substituted $C_{1-4}$ alkoxy, optionally-substituted $C_{1-4}$ dialkylamino, optionally-substituted $C_{6-10}$ aryl, optionally-substituted $C_{6-10}$ aryloxy, optionally-substituted 5- to 12-membered heteroaryl, optionally-substituted 5- to 12-membered heteroaryloxy, or hydroxy group. Preferably, $R^{10}R^{11}B—$ includes the following structures, but not limited thereto.

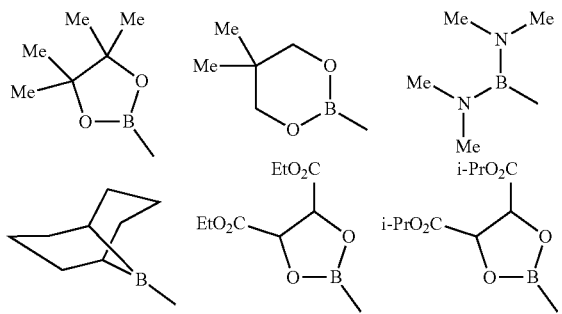

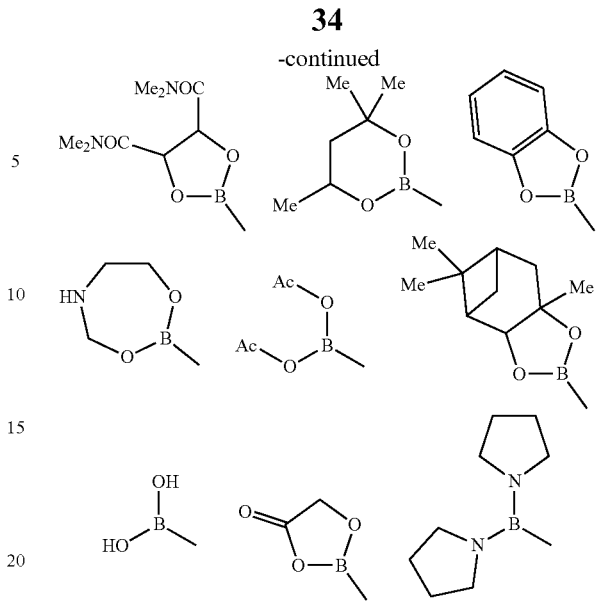

Step (5-1):

This step is a process to prepare boronate compound of formula (s-17) by reacting a compound of formula (s-15) and diborons such as bis(pinacolato)diboron in the presence of a catalyst and a base. The catalyst used herein includes [1,1'-bis(diphenylphosphino)ferrocene]dichloropalladium, tetrakis(triphenylphosphine)palladium, tris(dibenzylideneacetone)dipalladium, and dichlorobis(triphenylphosphine)palladium. The base used herein includes potassium acetate, tripotassium phosphate, and potassium carbonate. The solvent used herein includes 1,4-dioxane, toluene, and 1,2-dimethoxyethane. The reaction time is generally 1 hour to 48 hours, and the reaction temperature is room temperature to boiling point of a solvent used herein.

Step (5-2):

This step is a process to prepare a compound of formula (S-16) by reacting a boronate compound of formula (s-17) and a halide or triflate compound having $R^b$ group ($R^b$—$X^6$ ($X^6$: halogen atom) or $CF_3SO_2O$—$R^b$, etc.) in the presence of a catalyst and a base. For example, this step is Suzuki coupling reaction. The base used herein includes sodium carbonate, potassium carbonate, cesium carbonate, and tripotassium phosphate. The catalyst used herein includes palladium acetate, tetrakis(triphenylphosphine)palladium, and tris(dibenzylideneacetone)dipalladium. The solvent used herein includes 1,4-dioxane, toluene, and 1,2-dimethoxyethane. The reaction time is generally 30 minutes to 48 hours, and the reaction temperature is room temperature to boiling point of a solvent used herein.

A compound of formula (I) wherein any one or more of $R^{1a}$, $R^{1b}$, $R^{1c}$, and $R^{1d}$ are $R^b$ or a pharmaceutically acceptable salt thereof can be also prepared in the same manner as above.

Process 6:

The compound of formula (I) or (I') wherein $R^4$ is $R^{4a}$ (alkyl or cycloalkyl), i.e., Compound (S-19) or a pharmaceutically acceptable salt thereof can be prepared, for example, according to the following process.

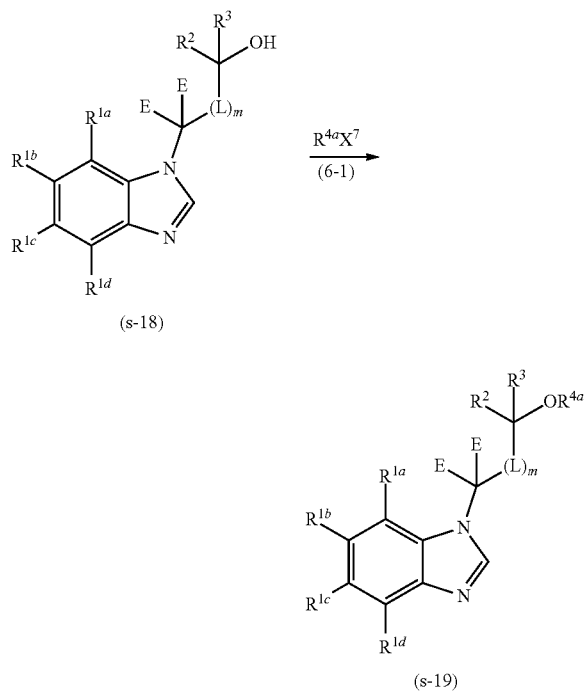

(s-18)

(s-19)

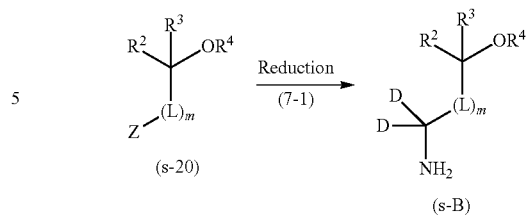

(s-20)

(s-B)

In the above scheme, E is the same or different and hydrogen or deuterium; $R^{1a}$, $R^{1b}$, $R^{1c}$, Rid, $R^2$, $R^3$, L, and m are as defined in Item 1; $X^7$ is the same definition as the above $X^1$; and $R^{4a}$ is the same as $R^4$, provided that hydrogen is excluded.

Step (6-1):

This step is a process to prepare a compound of formula (S-19) by reacting an alcohol compound (s-18) which is the compound of formula (I) wherein $R^4$ is hydrogen, and for example, a compound of $R^{4a}X^7$ in the presence of a base. The base used herein includes sodium hydride, potassium hydride, lithium hydride, n-butyllithium, and potassium tert-butoxide. The solvent used herein includes ethers such as diethyl ether and THF, DMF, NMP, and DMSO. The reaction time is generally 10 minutes to 24 hours, and the reaction temperature is 0° C. to boiling point of a solvent used herein.

The above-mentioned reduction of nitro group (Step (1-3), Step (3-3), Step (4-1)) and the subsequent cyclization (Step (1-4), Step (3-4), Step (4-2)) may be sequentially performed to proceed to the cyclization in one step, for example, formic acid or a formic acid equivalent such as orthoformate can be added to the reduction reaction of (s-3), (s-10), or (s-2) to prepare (S-5), (s-12), or (s-15). The reaction time of the sequential reactions is generally 10 minutes to 12 hours, and the reaction temperature is room temperature to boiling point of a solvent used herein.

Process 7:

In the above-mentioned amine compounds of (s-A), compound (s-B) wherein the both E are deuterium or chemically acceptable salt can be prepared, for example, according to the following process.

In the above scheme, $R^2$, $R^3$, $R^4$, L, and m are as defined in Item 1, Z is cyano group, carbamoyl group, or the like.

Step (7-1):

This step is a process to prepare an amine compound of formula (s-B) by reductive addition of deuterium to a compound of formula (s-20), which includes two reaction conditions, but should not be limited thereto.

1) A reaction condition herein using a reducing agent includes a step of reacting a compound of formula (s-20) with a reducing agent which is deuterated. The reducing agent which is deuterated includes sodium borodeuteride and lithium aluminum deuteride. The solvent used herein includes methanol, ether, and THF. The reaction time is generally 30 minutes to 10 hours, and the reaction temperature is 0° C. to boiling point of a solvent used herein.

2) A reaction condition herein using a catalyst includes a step of catalytically-reducing a compound of formula (s-20) under deuteration condition. The deuteration condition means "under deuterium atmosphere", "under pressured deuterium atmosphere", etc. The catalyst used herein includes palladium hydroxide-carbon and platinum oxide. The solvent used herein includes methanol, ethanol, THF, and ethyl acetate. The reaction time is generally 1 hour to 24 hours, and the reaction temperature is room temperature to boiling point of a solvent used herein.

In addition, an amine compound of formula (s-B) can be also prepared, for example, by using a deuterated starting material. Such deuterated starting material includes lycine-2,2-$^2H_2$.

The room temperature in the above processes means specifically 10° C. to 30° C.

The starting materials and intermediates in the above processes are known compounds or can be prepared from known compounds according to a known method. In case that any functional group other than a target reaction site can be reacted or can be unsuitable in the above processes, the functional group other than the target reaction site can be protected for the reaction, and the protective group can be cleaved to give a desired compound after the reaction is completed. The protective group used herein includes, for example, a conventional protective group disclosed in the aforementioned Protective Groups in Organic Synthesis and such. Specifically, the protective group for amino group includes, for example, ethoxycarbonyl, tert-butoxycarbonyl, acetyl, benzyl, and the like; and the protective group for hydroxy group includes, for example, tri-lower alkylsilyl, acetyl, benzyl, and the like.

The introduction and cleavage of protective groups can be done by a conventional method in organic chemistry (for example, see, the aforementioned Protective Groups in Organic Synthesis), or a similar method.

By appropriately changing functional group(s) in an intermediate or final product in the above processes, it is also possible to prepare a different compound defined in the present invention. The conversion of functional group(s) can be done according to a conventional method (e.g. Comprehensive Organic Transformations, R. C. Larock (1989)).

The intermediates and desired compounds in the above processes can be isolated/purified by a purification generally-used in synthetic organic chemistry, for example, neutralization, filtration, extraction, washing, drying, concentration, recrystallization, various chromatography, etc. Some intermediates can be used in next step without any purification.

The optical isomers of the present invention can be isolated by using a known division method at an appropriate step, for example, separation with an optically-active column, and fractionated crystallization. And, it is workable to use an optically-active starting material.

The compounds of the present invention may be sometimes an optical isomer, a stereoisomer, a tautomer such as a keto-enol compound, and/or a geometric isomer, hence which include all possible isomers including the above isomers, and a mixture thereof.

The compounds of the present invention may also include the compound of formula (I) or (I'), a prodrug thereof, and a pharmaceutically acceptable salt thereof, besides the above isomers. And, the compounds of the present invention or a pharmaceutically acceptable salt thereof may be in a form of an adduct with water or each solvent, hence which also include such adducts. In addition, the compounds of the present invention may also include various embodiments of the crystals and the compounds in which a part or all of atoms composing the compounds are replaced with another isotope (for example, replacing $^{12}C$ with $^{14}C$)

The term "prodrug of the compound of formula (I) or (I')" used herein means a compound which can be converted to the compound of formula (I) or (I') by reacting with an enzyme, gastric acid, etc. under intravitally physiological condition, i.e., a compound which can be enzymatically oxidized, reduced, hydrolyzed, or taken somehow to be converted to the compound of formula (I) or (I'), and a compound which can be hydrolyzed with gastric acid or the like to be converted to the compound of formula (I) or (I').

The "pharmaceutically acceptable salt" used herein includes, for example, a base addition salt or an acid addition salt. The base addition salt includes, for example, an alkali metal salt such as potassium salt and sodium salt; an alkaline earth metal salt such as calcium salt and magnesium salt; a water-soluble amine addition salt such as ammonium salt and N-methylglucamine (meglumine); and a lower alkanol ammonium salt of an organic amine. The acid addition salt includes, for example, hydrochloride, hydrobromide, hydroiodide, nitrate, sulfate, bisulfate, phosphate, acetate, lactate, citrate, tartrate, bitartrate, succinate, maleate, fumarate, gluconate, saccharate, benzoate, methanesulfonate, ethanesulfonate, benzene sulfonate, p-toluenesulfonate, and pamoate[1,1'-methylene-bis-(2-hydroxy-3-naphthoate)].

Salts of the present compound can be prepared, for example, in the following manners. For example, when the present compound is obtained in a salt form, the salt thereof can be prepared by directly purifying it. When the present compound is obtained in a free form, the salt thereof can be prepared by dissolving or suspending it in an appropriate organic solvent, adding a possible acid or base thereto, and then treating the obtained mixture in a general manner.

The compound of formula (I) or (I') prepared by the above processes may be isolated/purified in a conventional manner such as extraction, column chromatography, recrystallization, and reprecipitation. The extraction solvent used herein includes, for example, diethyl ether, ethyl acetate, chloroform, dichloromethane, toluene, and the like. The purification by column chromatography can be done with an acid-, basic-, or variously-chemical-treating silica gel, alumina, or the like. The elute solvent used herein includes, for example, hexane/ethyl acetate, hexane/chloroform, ethyl acetate/methanol, chloroform/methanol, acetonitrile/water, methanol/water, and the like.

The novel compounds of the present invention or a pharmaceutically acceptable salt thereof having a benzimidazole ring have a property inhibiting Nav 1.7 and thereby can be used as a medicament for treating or preventing a pain involving peripheral nerve such as C-fibres and Aδ-fibres, spontaneous pain such as numbness, burning pain, dull pain, pricking pain and shooting pain, neuropathic pain accompanied by hyperalgesia such as mechanical stimulation and cold stimulation or allodynia, nociceptive pain, inflammatory pain, small-fiber neuropathy, erythromelalgia, paroxysmal extreme pain disorder, etc. The neuropathic pain includes, for example, diabetic neuropathy, postherpetic neuralgia, chemotherapy-induced neuropathy, cancer pain, sensory nerve damage caused by viral infection in human immune deficiency syndrome, trigeminal neuralgia, complex regional pain syndrome, reflex sympathetic dystrophy, neuralgia after low back surgery, phantom limb pain, pain after spinal cord injury, persistent postoperative pain, inflammatory demyelinating polyradiculopathy, alcoholic neuropathy, entrapment peripheral neuropathy, iatrogenic neuropathy, sudden sensorineural disorder, malnutrition-induced neuropathy, radiation-induced neuropathy, radiculopathy, toxic peripheral neuropathy, traumatic peripheral neuropathy, brachial plexus avulsion injury, glossopharyngeal neuralgia, autoimmune neuropathy, and chronic cauda equina syndrome. The nociceptive pain or inflammatory pain includes low back pain, abdominal pain, chronic rheumatoid arthritis, a pain caused by osteoarthritis, myalgia, acute postoperative pain, fracture pain, pain after burn injury, and the like. In addition, the present compounds or a pharmaceutically acceptable salt thereof can be also used as a medicament for treating or preventing dysuria. The dysuria includes frequent urination, bladder pain caused by prostatic hyperplasia, and the like. Furthermore, the present compounds or a pharmaceutically acceptable salt thereof can be also used as a medicament for treating or preventing ataxia developed by suppressing abnormal nervous firing in the cerebellum in multiple sclerosis. In addition, the present compounds or a pharmaceutically acceptable salt thereof can be a drug having no side effect in heart or central nerve which is a problem in existing medication, since they have a selective inhibitory activity to Nav 1.7.

The present compounds may be administered orally, parenterally or rectally, and the daily dose can vary depending on the compound, the mode of administration, patient's condition/age, etc. For oral administration, for example, the present compounds may be administered generally in a dosage of about 0.01 to 1000 mg, preferably about 0.1 to 500 mg a day per kilogram of body weight of human or mammal and once to several times. For parenteral administration such as intravenous injection, for example, the present compounds may be administered generally in a dosage of about 0.01 to 300 mg, preferably about 1 to 100 mg per kilogram of body weight of human or mammal.

The present compounds can be orally or parenterally administered directly or as a suitable formulation comprising it. The formulation thereof may be, for example, tablet, capsule, powder, granule, liquid, suspension, injection, patch, gel patch, and the like, but not limited thereto. The formulation can be prepared with pharmaceutically acceptable additive agents in known means. The additive agents can be chosen for any purpose, including an excipient, a disintegrant, a binder, a fluidizer, a lubricant, a coating agent, a solubilizer, a solubilizing agent, a thickener, dispersant, a stabilizing agent, a sweetening agent, a flavor, and the like. Specifically, they include, for example, lactose, mannitol, microcrystalline cellulose, low-substituted hydroxypropylcellulose, cornstarch, partially-pregelatinized starch, carmellose calcium, croscarmellose sodium, hydroxypropylcellulose, hydroxypropyl methylcellulose, polyvinyl alcohol, magnesium stearate, sodium stearyl fumarate, polyethylene glycol, propylene glycol, titanium oxide, talc, and the like.

The present compounds and a pharmaceutically acceptable salt thereof may be used in combination with, for example, a non-steroidal anti-inflammatory agent such as celecoxib, Voltaren, ibuprofen, loxoprofen, acetaminophen, diclofenac and dexamethasone, and an opioid analgesic such as tramadol, morphine and oxycodone, in order to strengthen the action thereof. In addition, the present compounds and a pharmaceutically acceptable salt thereof may be also used in combination with an antiepileptic agent (such as pregabalin and carbamazepine), an aldose reductase inhibitor (such as epalrestat), a prostaglandin derivative drug (such as limaprost alfadex), an antidepressive agent (such as amitriptyline and duloxetine), an anticonvulsant agent, an anxiolytic agent, a dopamine receptor agonist, an antiparkinsonian agent, a hormone preparation, a migraine medication, an adrenergic P receptor antagonist, a drug for treating dementia, a drug for treating mood disorder, or the like. Preferred drugs used in combination with the present compound and a pharmaceutically acceptable salt thereof include an antiepileptic agent such as pregabalin and carbamazepine, an antidepressive agent such as amitriptyline and duloxetine, a narcotic analgesic such as morphine, oxycodone and tramadol, an anti-inflammatory agent such as acetaminophen, diclofenac and dexamethasone, an aldose reductase inhibitor such as epalrestat, and a prostaglandin derivative such as limaprost alfadex. In order to reduce the side effects thereof, the present compounds and a pharmaceutically acceptable salt thereof may be used in combination with an antiemetic drug and a sleep-inducing drug. The administration interval of the present compound and its concomitant drug is not limited, i.e., the concomitant drug may be administered at the same time as the present compound or at a suitable interval. Or, the present compound and its concomitant drug can be formulated into a combination drug. The dose of the combination drug can be suitably determined based on the standard of the clinically-used dose thereof. The combination ratio of the present compound and its concomitant drug can be suitably determined based on its subject patient, administration route, disease, pathology, concomitant drug, etc. For example, when the subject patient is a human being, the concomitant drug may be used in 0.01 to 1000 part by weight per part of the present compound.

EXAMPLES

The present invention is explained in more detail in the following by referring to Reference examples, Comparative examples, Examples, and Tests; however, the technical scope of the present invention is not limited to such Examples and the like. The silica gel chromatography used in Reference example, Comparative examples, and Examples was silica gel column chromatography or amino silica gel column chromatography made by YAMAZEN CORPORATION. Each compound was identified with a proton nuclear magnetic resonance spectrum ($^1$H-NMR). $^1$H-NMR was measured with JNM-ECS400 (JEOL).

Unless otherwise specified, the starting material compounds, reaction reagents and solvents used herein were commercially available products or were prepared according to known methods.

In Processes, Reference examples, Comparative examples, Examples, and Tests, abbreviations shown below may be sometimes used to simplify the description of the present specification. Me: methyl, THF: tetrahydrofuran, DMF: N,N-dimethylformamide, NMP: N-methyl-2-pyrrolidinone, DMSO: dimethylsulfoxide, HEPES: 2-[4-(2-hydroxyethyl)-1-piperazinyl]ethanesulfonic acid, EGTA: O,O'-bis(2-aminoethyl)ethylene glycol-N,N,N',N'-tetraacetate, NADPH: nicotinamide adenine dinucleotide phosphate, LC: liquid chromatography, MS: mass spectrography, NMR: nuclear magnetic resonance, D: deuterium, $^2$H: deuterium, J: coupling constant, s: singlet, d: doublet, t: triplet, dd: double doublet, m: multiplet, br: broad.

Reference Example 1: Preparation of 1-amino-2-methyl(1,1-$^2$H$_2$)propan-2-ol monohydrochloride (Compound 5)

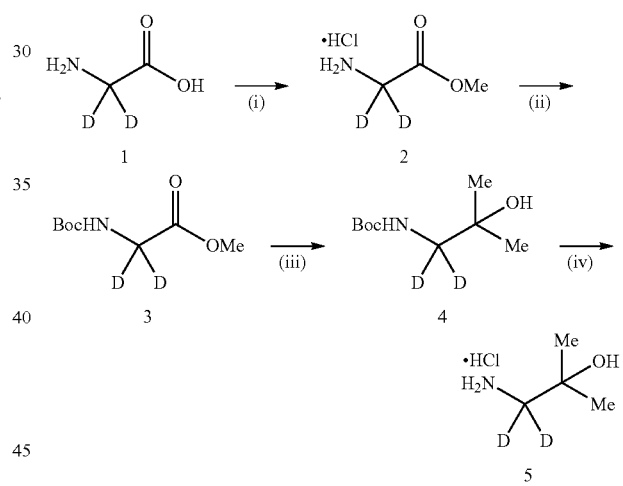

Step (i):

To a mixture of glycine-2,2-$^2$H$_2$ (Compound 1, 5.0 g) and methanol (75 mL) was added thionyl chloride (7.4 mL) at 0° C., and the mixture was stirred at 50° C. for 4 hours. The reaction solution was cooled to room temperature and concentrated in vavuo, and the residue was azeotropic dried with methanol. The obtained residue was slurry-washed with ethyl acetate to give Compound 2 (8.2 g).

Step (ii):

To a mixture of Compound 2 (8.0 g) and THF (75 mL) were added triethylamine (19.2 mL) and di-tert-butyl dicarbonate (13.7 g), and the mixture was stirred at 50° C. for 3 hours. The reaction mixture was cooled to room temperature and filtrated, and the filtrate was concentrated in vavuo. The residue was dissolved in ethyl acetate, and the solution was washed with aqueous sodium bicarbonate and water. The organic layer was dried over sodium sulfate, and then concentrated in vavuo to give Compound 3 as a crude product (11.3 g).

Step (iii):

To a solution of a crude product of Compound 3 (11.2 g) in THF (78 mL) was added methylmagnesium bromide/diethyl ether solution (3.0 mol/L, 78 mL) dropwise at 0° C. over 3 hours, and the mixture was stirred at room temperature for 3 more hours. Aqueous ammonium chloride and ethyl acetate were added to the reaction mixture to separate layers. The organic layer was washed with water and dried over sodium sulfate, and then concentrated in vavuo to give Compound 4 as a crude product (10.7 g).

Step (iv):

To a solution of a crude product of Compound 4 (10.6 g) in ethyl acetate (25 mL) was 4 mol/L hydrochloric acid/ethyl acetate solution (50 mL), and the mixture was stirred at room temperature for 4 hours. The reaction solution was concentrated in vavuo, and the residue was azeotropic dried with methanol to give 1-amino-2-methyl (1,1-$^2$H$_2$)propan-2-ol (Compound 5) as a crude product (7.0 g).

Reference Example 2: Preparation of 1-amino-2-methyl(1,1-$^2$H$_2$)propan-2-ol (Compound 7)

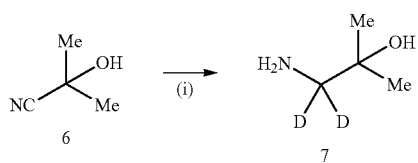 [SMILES: CC(C)(O)C#N ; [2H]C([2H])(N)C(C)(C)O]

Step (i):

To a mixture of lithium aluminum deuteride (1.0 g) and THF (20 mL) was added a solution of acetone cyanohydrin (Compound 6, 1.0 g) in THF (10 mL) dropwise at 0° C. over 30 minutes, and the mixture was stirred at room temperature for 3 hours. To the reaction solution was added sodium sulfate decahydrate (6.0 g), and the mixture was stirred at room temperature overnight. The reaction mixture was filtrated with Celite, and then the filtrate was concentrated in vavuo to give 1-amino-2-methyl(1,1-$^2$H$_2$)propan-2-ol (Compound 7) as a crude product (0.9 g).

Alternatively, Compound 7 can be prepared with 2-methyl-2-hydroxypropionamide (Compound 8) and lithium aluminum deuteride in a similar manner.

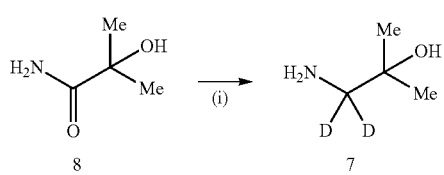 [SMILES: CC(C)(O)C(N)=O ; [2H]C([2H])(N)C(C)(C)O]

Reference Example 3: Preparation of 4-amino-2-methyl(4,4-$^2$H$_2$)butan-2-ol (Compound 11)

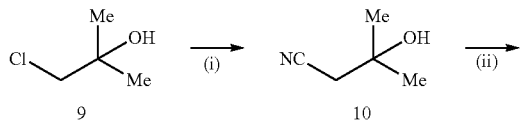

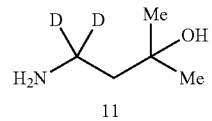

Step (i):

To a mixture of 1-chloro-2-methyl-propan-2-ol (Compound 9, 523 mg), ethanol (10 mL), and distilled water (2.0 mL) was added sodium cyanide (283 mg), and the mixture was stirred under reflex for 3 hours. The reaction mixture was cooled to room temperature, and ethyl acetate and water were added thereto to separate layers. The organic layer was dried over sodium sulfate and concentrated in vavuo to give Compound 10 (250 mg).

Step (ii):

To a mixture of lithium aluminum deuteride (159 mg) and THF (10 mL) was added a solution of Compound 10 (1.0 g) in THF (5.0 mL) dropwise at 0° C., and the mixture was stirred at room temperature for 3 more hours. To the reaction solution was added sodium sulfate decahydrate (6.0 g), and the mixture was stirred at room temperature overnight. The reaction mixture was filtrated with Celite, and then the filtrate was concentrated in vavuo to give 4-amino-2-methyl (4,4-$^2$H$_2$)butan-2-ol (Compound 11) as a crude product (240 mg).

Reference Example 4: Preparation of 3-[amino($^2$H$_2$)methyl]oxetan-3-ol (Compound 14)

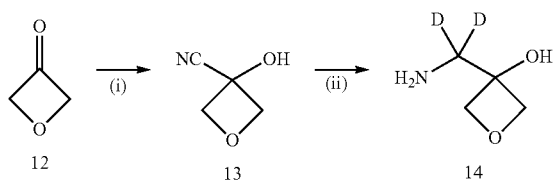 [SMILES: O=C1COC1 ; N#CC1(O)COC1 ; [2H]C([2H])(N)C1(O)COC1]

Step (i):

A mixture of oxetan-3-one (Compound 12, 464 mg), lithium perchlorate (685 mg), and trimethylsilyl cyanide (1.0 mL) was stirred at room temperature for 2 hours. To the reaction mixture was added chloroform, and the mixture was filtrate. Then, the organic layer was washed with water, dried over sodium sulfate, and then concentrated in vavuo to give Compound 13 as a crude product (808 mg).

Step (ii):

To a suspension of lithium aluminum deuteride (297 mg) and THF (10 mL) was added a solution of Compound 13 (808 mg) in THF (10 mL) dropwise at 0° C., and the mixture was stirred at room temperature for 5 hours. To the reaction solution was added sodium sulfate decahydrate (2.0 g), and the mixture was stirred at room temperature overnight. The reaction mixture was filtrated with Celite, and the filtrate was concentrated in vavuo to give 3-[amino($^2$H$_2$)methyl]oxetan-3-ol (Compound 14) as a crude product (632 mg).

Reference Example 5: Preparation of 6-(4-fluorophenoxy)-1H-benzimidazole (Compound 18)

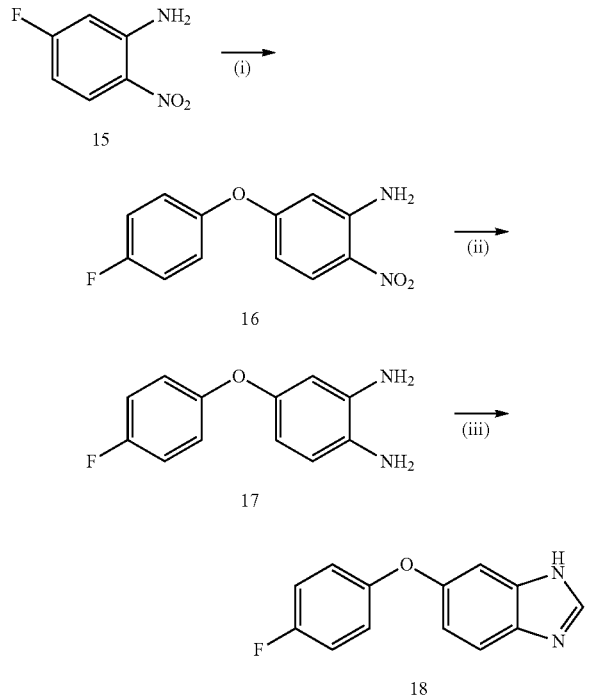

Step (i):

A mixture of 5-fluoro-2-nitroaniline (Compound 15, 100 mg), cesium carbonate (313 mg), 4-fluorophenol (86 mg), and NMP (1.0 mL) was stirred at 100° C. for 1 hour. The reaction mixture was cooled to room temperature, and ethyl acetate and water were added thereto to separate layers. The organic layer was washed with water, dried over sodium sulfate, and then concentrated in vavuo. The obtained residue was purified by silica gel column chromatography (eluting solution:hexane/ethyl acetate=1/1) to give Compound 16 (124 mg).

Step (ii):

A mixture of Compound 16 (124 mg), palladium-carbon (120 mg), and THF (5.0 ml) was stirred under hydrogen atmosphere at room temperature for 2 hours. The reaction solution was filtrated with Celite, and the filtrate was concentrated in vavuo to give Compound 17 (106 mg).

Step (iii):

A mixture of Compound 17 (106 mg), p-toluenesulfonic acid monohydrate (10 mg), trimethyl orthoformate (0.3 ml), and methanol (5.0 ml) was stirred at room temperature for 2 hours, and then at 50° C. for 1 hour. The reaction mixture was cooled to room temperature and concentrated in vavuo. The obtained residue was purified by silica gel column chromatography (eluting solution:chloroform/methanol=20/1) to give 6-(4-fluorophenoxy)-1H-benzimidazole (Compound 18, 82 mg).

Reference Example 6: Preparation of 6-{[5-(trifluoromethyl)pyridin-2-yl]oxy}-1H-benzimidazole (Compound 21)

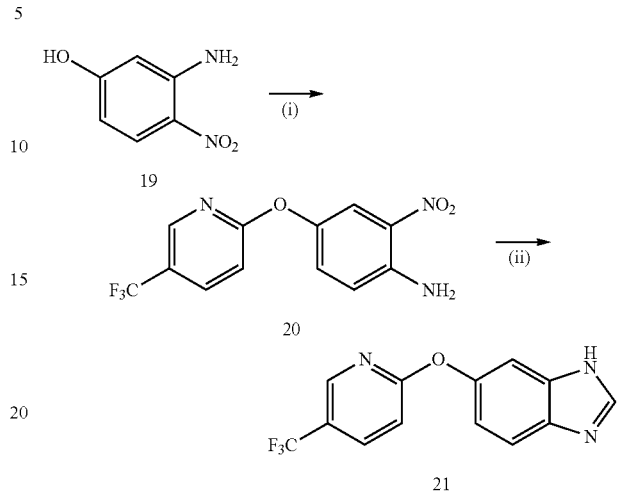

Step (i):

A mixture of 4-amino-3-nitrophenol (Compound 19, 200 mg), cesium carbonate (458 mg), 2-fluoro-5-(trifluoromethyl)pyridine (130 μL), and NMP (2.0 mL) was stirred at room temperature for 6 hours. Ethyl acetate and water were added to the reaction mixture to separate layers. The organic layer was washed with water, dried over sodium sulfate, and then concentrated in vavuo. The obtained residue was purified by silica gel column chromatography (eluting solution: chloroform/methanol=20/1) to give Compound 20 (320 mg).

Step (ii):

To a solution of Compound 20 (320 mg) in methanol (6.0 mL) were added formic acid (0.4 mL), trimethyl orthoformate (3.0 mL), and zinc powder (354 mg), and the mixture was stirred at 60° C. for 2 hours. The reaction mixture was cooled to room temperature, and aqueous sodium bicarbonate and ethyl acetate were added thereto. The mixture was filtrated with Celite, and the filtrate was separated into layers. The organic layer was dried over sodium sulfate and concentrated in vavuo. The obtained residue was purified by silica gel column chromatography (eluting solution:chloroform/methanol=30/1) to give 6-{[5-(trifluoromethyl)pyridin-2-yl]oxy}-1H-benzimidazole (Compound 21, 135 mg).

Reference Example 7: Preparation of 6-(4-chlorophenoxy)-1H-benzimidazole (Compound 24)

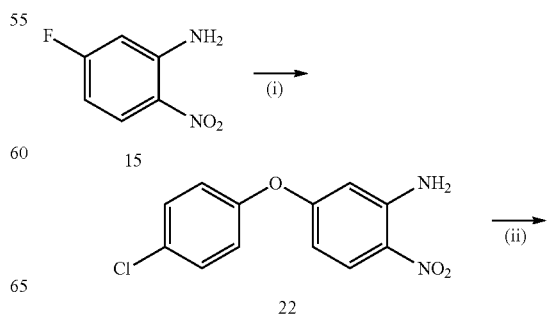

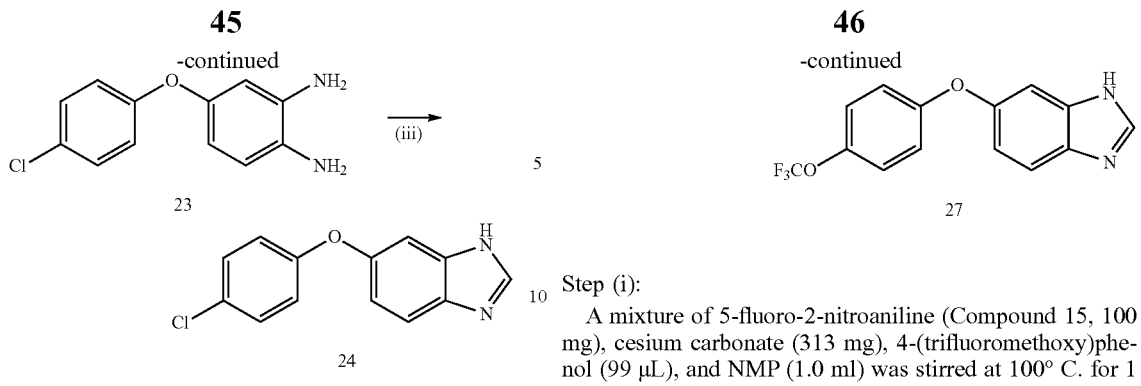

Step (i):
A mixture of 5-fluoro-2-nitroaniline (Compound 15, 100 mg), cesium carbonate (313 mg), 4-chlorophenol (99 mg), and NMP (1.0 ml) was stirred at 100° C. for 1 hour. The reaction mixture was cooled to room temperature, and ethyl acetate and water were added thereto to separate layers. The organic layer was washed with water, dried over sodium sulfate, and then concentrated in vavuo. The obtained residue was purified by silica gel column chromatography (eluting solution:hexane/ethyl acetate=1/1) to give Compound 22 (136 mg).

Step (ii):
A mixture of Compound 22 (136 mg), platinum sulfide on carbon (130 mg), and THF (5.0 ml) was stirred under hydrogen atmosphere at room temperature for 6 hours. The reaction solution was filtrated with Celite and concentrated in vavuo to give Compound 23 (120 mg).

Step (iii):
A mixture of Compound 23 (120 mg), p-toluenesulfonic acid monohydrate (10 mg), trimethyl orthoformate (0.3 ml), and methanol (5.0 ml) was stirred at room temperature for 2 hours, and then at 50° C. for 1 hour. The reaction mixture was cooled to room temperature and concentrated in vavuo. The obtained residue was purified by silica gel column chromatography (eluting solution:chloroform/methanol=20/1) to give 6-(4-chlorophenoxy)-1H-benzimidazole (Compound 24, 88 mg).

Reference Example 8: Preparation of 6-[4-(trifluoromethoxy)phenoxy]-1H-benzimidazole (Compound 27)

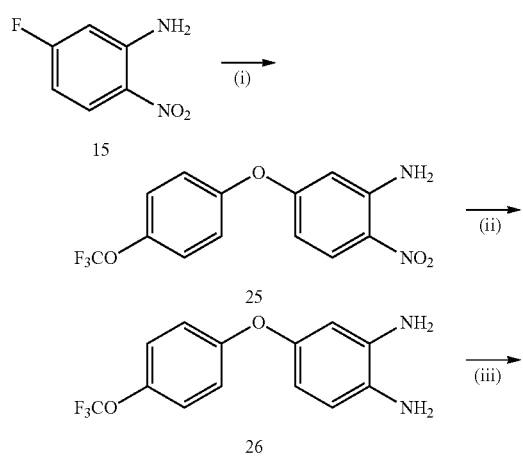

Step (i):
A mixture of 5-fluoro-2-nitroaniline (Compound 15, 100 mg), cesium carbonate (313 mg), 4-(trifluoromethoxy)phenol (99 μL), and NMP (1.0 ml) was stirred at 100° C. for 1 hour. The reaction mixture was cooled to room temperature, and ethyl acetate and water were added thereto to separate layers. The organic layer was washed with water, dried over sodium sulfate, and then concentrated in vavuo. The obtained residue was purified by silica gel column chromatography (eluting solution:hexane/ethyl acetate=1/1) to give Compound 25 (175 mg).

Step (ii):
A mixture of Compound 25 (175 mg), palladium-carbon (150 mg), and THF (5.0 ml) was stirred under hydrogen atmosphere at room temperature for 6 hours. The reaction solution was filtrated with Celite and concentrated in vavuo to give Compound 26 (152 mg).

Step (iii):
A mixture of Compound 26 (120 mg), p-toluenesulfonic acid monohydrate (10 mg), trimethyl orthoformate (0.3 ml), and methanol (5.0 ml) was stirred at room temperature for 2 hours, and then at 50° C. for 1 hour. The reaction mixture was cooled to room temperature and concentrated in vavuo. The obtained residue was purified by silica gel column chromatography (eluting solution:chloroform/methanol=20/1) to give 6-[4-(trifluoromethoxy)phenoxy]-1H-benzimidazole (Compound 27, 124 mg).

Reference Example 9: Preparation of 6-[2-methoxy-4-(trifluoromethyl)phenyl]-1H-benzimidazole (Compound 29)

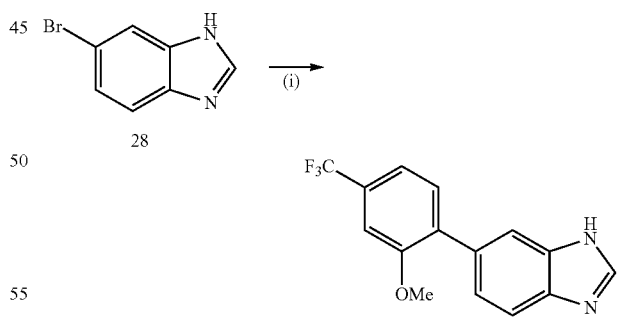

Step (i):
A mixture of 6-bromobenzimidazole (Compound 28, 100 mg), 2-methoxy-4-(trifluoromethyl)phenylboronic acid (167 mg), tetrakis(triphenylphosphine)palladium (26 mg), potassium carbonate (210 mg), 1,4-dioxane (2.0 mL), and distilled water (0.5 mL) was stirred at 100° C. for 1 hour. The reaction solution was cooled to room temperature, charged on silica gel and purified by silica gel column chromatography (eluting solution:chloroform/methanol=20/1) to give 6-[2-methoxy-4-(trifluoromethyl)phenyl]-1H-benzimidazole (Compound 29, 86 mg).

Comparative Example 1: Preparation of 1-[6-(4-fluorophenoxy)-1H-benzimidazol-1-yl]-2-methylpropan-2-ol

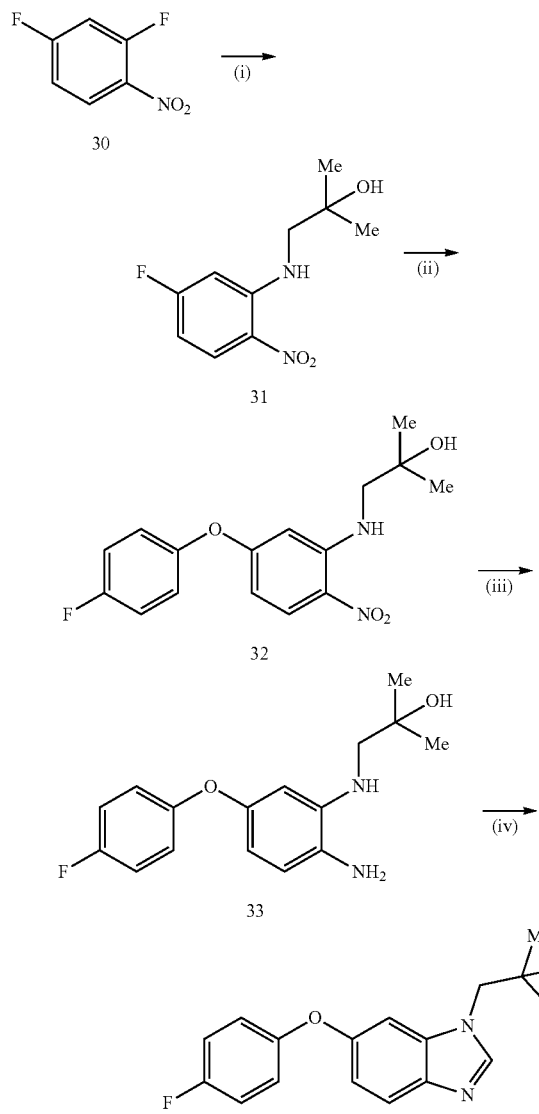

Step (i):
A mixture of 2,4-difluoro-1-nitrobenzene (Compound 30, 1.6 g), 1-amino-2-methylpropan-2-ol (1.0 g), diisopropylethylamine (5.2 mL), and DMF (50 mL) was stirred at 60° C. for 2 hours. The reaction mixture was cooled to room temperature, and water, ethyl acetate, and hexane were added thereto to separate layers. The organic layer was washed with water, dried over sodium sulfate, and then concentrated in vavuo to give Compound 31 as a crude product.

Step (ii):
A mixture of a crude product of Compound 31, 4-fluorophenol (1.7 g), cesium carbonate (6.5 g), and NMP (25 mL) was stirred at 100° C. for 2 hours. The reaction mixture was cooled to room temperature, and water, ethyl acetate, and hexane were added thereto to separate layers. The organic layer was washed with water, dried over sodium sulfate, and then concentrated in vavuo. The obtained residue was purified by silica gel column chromatography (eluting solution:hexane/ethyl acetate=3/1) to give Compound 32 (3.1 g).

Step (iii):
A mixture of Compound 32 (3.1 g), ammonium formate (3.0 g), palladium-carbon (0.30 g), and methanol (47 mL) was stirred at 50° C. for 2 hours. The reaction mixture was cooled to room temperature, filtrated with Celite, and concentrated in vavuo. Saturated aqueous sodium bicarbonate and ethyl acetate were added to the residue to separate layers. The organic layer was washed with water, dried over sodium sulfate, and then concentrated in vavuo. The obtained residue was purified by silica gel column chromatography (eluting solution:chloroform/methanol=99/1) to give Compound 33 (2.7 g).

Step (iv):
A mixture of Compound 33 (600 mg), trimethyl orthoformate (1.7 mL), and p-toluenesulfonic acid monohydrate (79 mg) was stirred at 60° C. for 1 hour. The reaction mixture was cooled to room temperature, and saturated aqueous sodium bicarbonate and ethyl acetate were added thereto to separate layers. The organic layer was washed with water, dried over sodium sulfate, and then concentrated in vavuo. The obtained residue was purified by silica gel column chromatography (eluting solution:chloroform/methanol=95/5) to give 1-[6-(4-fluorophenoxy)-1H-benzimidazol-1-yl]-2-methylpropan-2-ol (410 mg).
$^1$H-NMR (DMSO-d6) δ: 1.06 (6H, s), 4.08 (2H, s), 4.72 (1H, s), 6.87 (1H, m), 6.96-6.99 (2H, m), 7.17 (2H, m), 7.39 (1H, m), 7.62 (1H, m), 8.09 (1H, s).

Comparative Example 2: Preparation of 2-methyl-1-(6-{[5-(trifluoromethyl)pyridin-2-yl]oxy}-1H-benzimidazol-1-yl)propan-2-ol

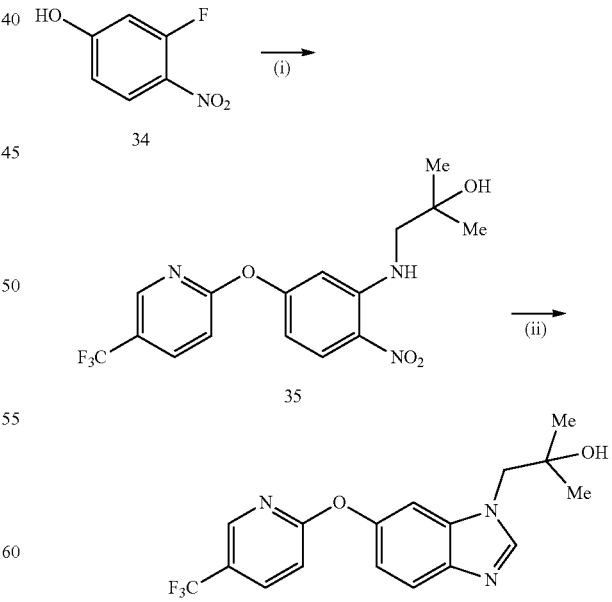

Step (i):
A mixture of 3-fluoro-4-nitrophenol (Compound 34, 1.0 g), diisopropylethylamine (2.1 g), 1-amino-2-methylpropan-2-ol (0.7 g), and NMP (16 mL) was stirred at 100° C. for 4 hours. To the reaction mixture were added cesium carbonate (3.1 g) and 2-fluoro-5-(trifluoromethyl)pyridine (1.4 g), and the mixture was stirred at 100° C. for 3 hours. The reaction mixture was cooled to room temperature, and water, ethyl acetate, and hexane were added thereto to separate layers. The organic layer was washed with water, dried over sodium sulfate, and then concentrated in vavuo. The obtained residue was slurry-washed with hexane/ethyl acetate (=9/1) to give Compound 35 (1.5 g).

Step (ii):

To a solution of Compound 35 (500 mg) in methanol (7.0 ml) were added formic acid (0.5 mL), trimethyl orthoformate (3.7 mL), and zinc (440 mg), and the mixture was stirred at 70° C. for 2 hours. The reaction solution was cooled to room temperature and filtrated with Celite. The filtrate was concentrated in vavuo, and ethyl acetate and aqueous Rochelle salt were added to the residue to separate layers. The organic layer was washed with water, dried over sodium sulfate, and concentrated in vavuo. The obtained residue was recrystallized with hexane/ethyl acetate (=1:5) to give 2-methyl-1-(6-{[5-(trifluoromethyl)pyridin-2-yl]oxy}-1H-benzimidazol-1-yl)propan-2-ol (330 mg).

$^1$H-NMR (DMSO-d6) δ: 1.07 (6H, s), 4.11 (2H, s), 4.73 (1H, s), 7.00 (1H, m), 7.18 (1H, m), 7.56 (1H, m), 7.66 (1H, m), 8.13 (1H, s), 8.20 (1H, m), 8.54 (1H, m)

Comparative Example 3: Preparation of 4-[6-(4-chlorophenoxy)-1H-benzimidazol-1-yl]-2-methylbutan-2-ol

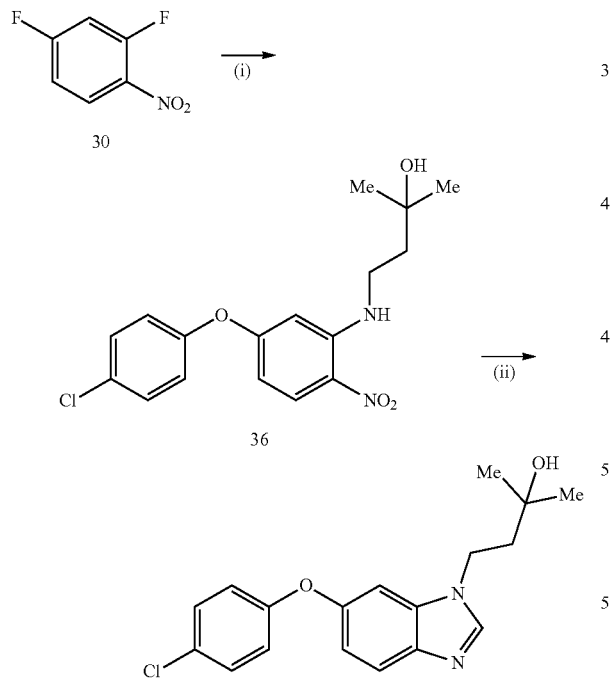

Step (i):

A mixture of 2,4-difluoro-1-nitrobenzene (Compound 30, 200 mg), 4-amino-2-methylbutan-2-ol (136 mg), diisopropylethylamine (263 μL), and NMP (2.0 mL) was stirred at 110° C. for 30 minutes. To the reaction mixture were added cesium carbonate (819 mg) and 4-chlorophenol (186 mg), and the mixture was stirred at 150° C. for 3 hours. The reaction mixture was cooled to room temperature, and ethyl acetate and water were added thereto to separate layers. The organic layer was washed with water, dried over sodium sulfate, and then concentrated in vavuo. The obtained residue was purified by silica gel column chromatography (eluting solution:hexane/ethyl acetate=1/1) to give Compound 36 (350 mg).

Step (ii):

To a solution of Compound 36 (350 mg) in methanol (5.0 mL) were added formic acid (0.4 mL), trimethyl orthoformate (2.8 mL), and zinc powder (326 mg), and the mixture was stirred at 60° C. for 3 hours. The reaction solution was cooled to room temperature and filtrated with Celite, and concentrated in vavuo. The obtained residue was purified by silica gel column chromatography (eluting solution:chloroform/methanol=20/1).

The obtained crude product was recrystallized with hexane/ethyl acetate (=1:1) to give 4-[6-(4-chlorophenoxy)-1H-benzimidazol-1-yl]-2-methylbutan-2-ol (237 mg).

$^1$H-NMR (CDCl$_3$) δ: 1.30 (6H, s), 1.99-2.03 (2H, m), 4.28-4.32 (2H, m), 6.90-6.91 (2H, m), 6.98 (1H, dd, J=8.5, 2.4 Hz), 7.07 (1H, d, J=2.4 Hz), 7.26-7.27 (2H, m), 7.75 (1H, d, J=9.2 Hz), 8.12 (1H, br s).

Comparative Example 4: Preparation of 3-({6-[4-(trifluoromethoxy)phenoxy]-1H-benzimidazol-1-yl}methyl)oxetan-3-ol

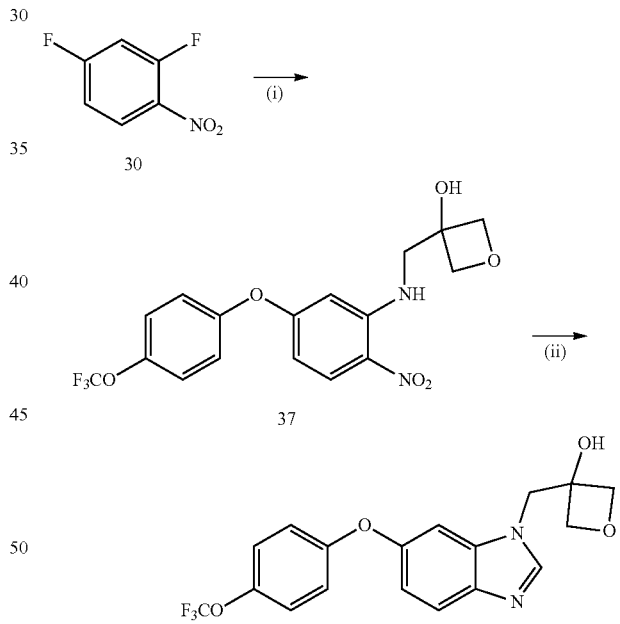

Step (i):

A mixture of 2,4-difluoro-1-nitrobenzene (Compound 30, 17.1 g), 3-(aminomethyl)oxetan-3-ol (11.7 g), diisopropylethylamine (24.2 mL), and NMP (110 mL) was stirred at room temperature for 2 hours. To the reaction mixture were added cesium carbonate (45.6 g) and 4-(trifluoromethoxy)phenol (14.6 mL), and the mixture was stirred at 120° C. for 4 hours. The reaction mixture was cooled to room temperature, and ethyl acetate and water were added thereto to separate layers. The organic layer was washed with water, dried over sodium sulfate, and then concentrated in vavuo. The obtained residue was purified by silica gel column chromatography (eluting solution:ethyl acetate). The crude product was slurry-washed with hexane/ethyl acetate (=3/1) to give Compound 37 (10.2 g).

Step (ii):

To a solution of Compound 37 (659 mg) in methanol (8.0 mL) were added formic acid (0.6 mL), trimethyl orthoformate (4.5 mL), and zinc powder (538 mg), and the mixture was stirred at 60° C. for 2 hours. The reaction solution was cooled to room temperature, filtrated with Celite, and concentrated in vavuo. The obtained residue was purified by silica gel column chromatography (eluting solution:chloroform/methanol=20/1). The crude product was slurry-washed with hexane/ethyl acetate (=1:1) to give 3-({6-[4-(trifluoromethoxy)phenoxy]-1H-benzimidazol-1-yl}methyl)oxetan-3-ol (306 mg).

$^1$H-NMR (CDCl$_3$) δ: 3.82 (1H, br s), 4.49 (2H, s), 4.55-4.63 (4H, m), 6.92-6.96 (3H, m), 7.14 (2H, d, J=8.6 Hz), 7.20 (1H, d, J=1.8 Hz), 7.62 (1H, d, J=8.6 Hz), 7.94 (1H, s).

Comparative Example 5: Preparation of 3-({6-[2-methoxy-4-(trifluoromethyl)phenyl]-1H-benzimidazol-1-yl}methyl)oxetan-3-ol

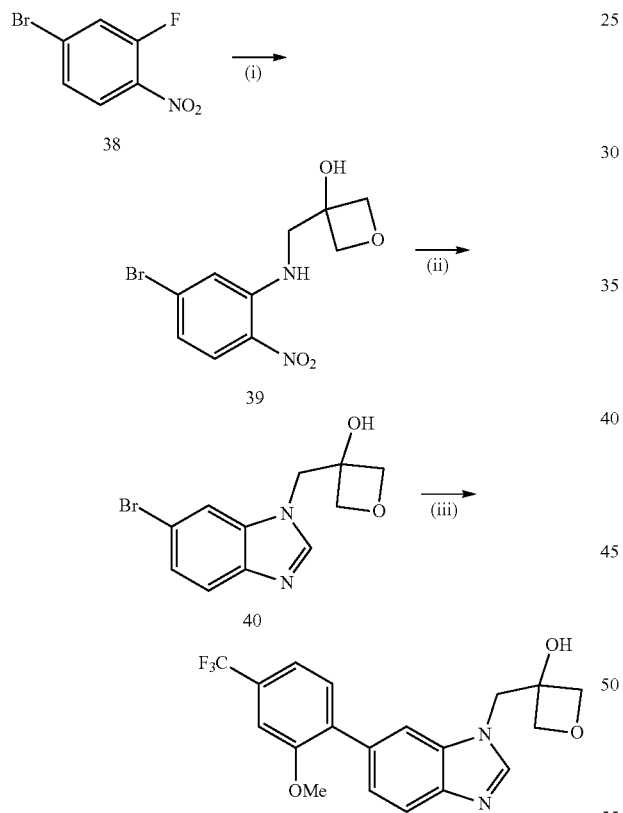

Step (i):

A mixture of 4-bromo-2-fluoro-1-nitrobenzene (Compound 38, 26.2 g), 3-(aminomethyl)oxetan-3-ol (12.3 g), diisopropylethylamine (31.2 mL), and NMP (180 mL) was stirred at 100° C. for 3 hours. The reaction mixture was cooled to room temperature, and ethyl acetate and water were added thereto to separate layers. The organic layer was washed with water, dried over sodium sulfate, and then concentrated in vavuo. The obtained residue was slurry-washed with hexane/chloroform (=3/2) to give Compound 39 (29.8 g).

Step (ii):

To a solution of Compound 39 (22.0 g) in methanol (200 mL) were added formic acid (27.8 mL), trimethyl orthoformate (120 mL), and zinc powder (15.7 g), and the mixture was stirred at room temperature for 1 hour. The reaction solution was filtrated with Celite and concentrated in vavuo. Ethyl acetate and aqueous Rochelle salt were added to the obtained residue to separate layers. The organic layer was washed with water, dried over sodium sulfate, and concentrated in vavuo. The obtained residue was slurry-washed with heptane/2-propanol (=4/3) to give Compound 40 (19.1 g).

Step (iii):

A mixture of Compound 40 (13.9 g), 2-methoxy-4-(trifluoromethyl)phenylboronic acid (16.2 g), tetrakis(triphenylphosphine)palladium (5.7 g), potassium carbonate (20.4 g), 1,2-dimethoxyethane (180 mL), and distilled water (60 mL) was stirred at 80° C. for 2 hours. The reaction mixture was cooled to room temperature, and ethyl acetate and water were added thereto to separate layers. The organic layer was washed with water, dried over sodium sulfate, and then concentrated in vavuo. The obtained residue was purified by silica gel column chromatography (eluting solution:chloroform/methanol=20/1). The obtained crude product was recrystallized with heptane/2-propanol (=2/1) to give 3-({6-[2-methoxy-4-(trifluoromethyl)phenyl]-1H-benzimidazol-1-yl}methyl)oxetan-3-ol (10.60 g).

$^1$H-NMR (DMSO-d6) δ: 3.84 (3H, s), 4.42 (2H, d, J=6.7 Hz), 4.54 (2H, d, J=6.7 Hz), 4.59 (2H, s), 6.22 (1H, s), 7.33 (1H, dd, J=8.2, 1.5 Hz), 7.37-7.41 (2H, m), 7.55 (1H, d, J=7.9 Hz), 7.66 (1H, d, J=8.5 Hz), 7.84 (1H, s), 8.28 (1H, s).

Example 1: Preparation of 1-[6-(4-fluorophenoxy)-1H-benzimidazol-1-yl]-2-methyl (1,1-$^2$H$_2$) propan-2-ol

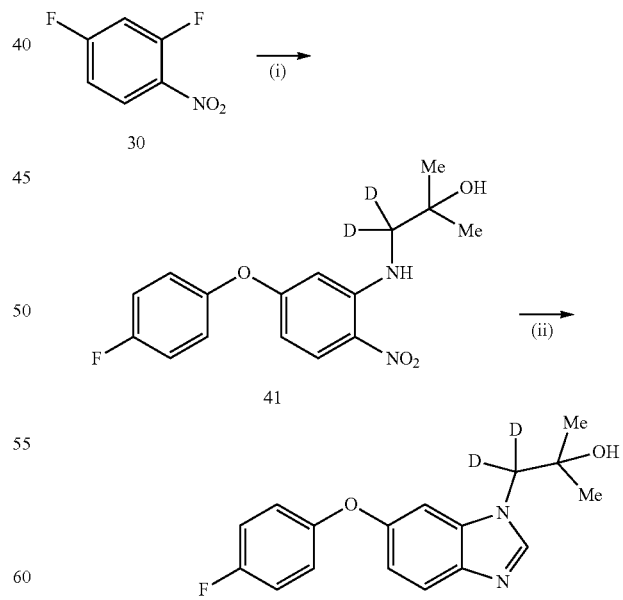

Step (i):

A mixture of 2,4-difluoro-1-nitrobenzene (Compound 30, 1.1 g), a crude product of Compound 5 (Reference example 1) (1.2 g), diisopropylethylamine (2.8 mL), and NMP (12 mL) was stirred at room temperature for 1 hour. Cesium carbonate (3.2 g) and 4-fluorophenol (1.0 g) were added to the reaction mixture, and the mixture was stirred at 100° C. for 4 hours. The reaction mixture was cooled to room temperature, and ethyl acetate and water were added thereto to separate layers. The organic layer was washed with water, dried over sodium sulfate, and then concentrated in vavuo. The obtained residue was purified by silica gel column chromatography (eluting solution:hexane/ethyl acetate=1/1) to give Compound 41 as a crude product (2.7 g).

Step (ii):

To a solution of a crude product of Compound 41 (2.7 g) in methanol (30 mL) were added formic acid (2.5 mL), trimethyl orthoformate (14.6 mL), and zinc powder (2.2 g), and the mixture was stirred at room temperature for 1 hour. The reaction solution was filtrated with Celite and concentrated in vavuo. The obtained residue was purified by silica gel column chromatography (eluting solution:chloroform/methanol=20/1). The crude product was slurry-washed with hexane/ethyl acetate (=1:1) to give 1-[6-(4-fluorophenoxy)-1H-benzimidazol-1-yl]-2-methyl(1,1-$^2$H$_2$)propan-2-ol (960 mg).

$^1$H-NMR (DMSO-d6) δ: 1.06 (6H, s), 4.72 (1H, s), 6.87 (1H, dd, J=8.5, 2.4 Hz), 6.96-7.00 (2H, m), 7.14-7.20 (2H, m), 7.39 (1H, d, J=2.4 Hz), 7.62 (1H, d, J=8.5 Hz), 8.08 (1H, s).

Example 2: Preparation of 2-methyl-1-(6-{[5-(trifluoromethyl)pyridin-2-yl]oxy}-1H-benzimidazol-1-yl) (1,1-$^2$H$_2$)propan-2-ol

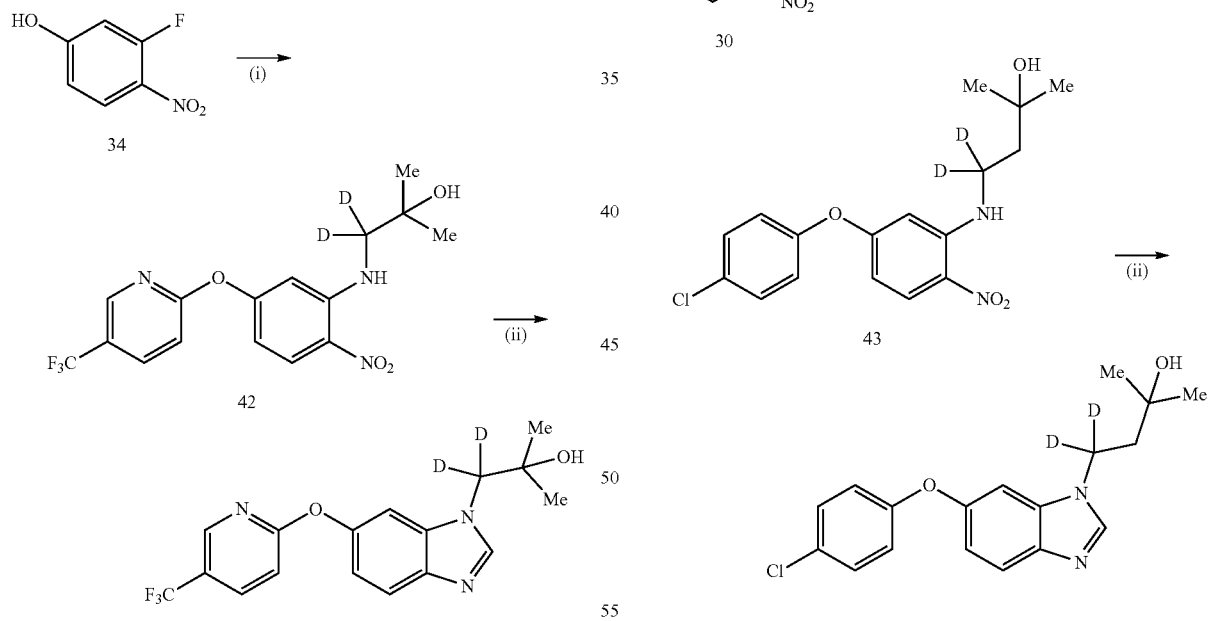

Step (i):

A mixture of 3-fluoro-4-nitrophenol (Compound 34, 2.1 g), a crude product of Compound 5 (Reference example 1) (2.0 g), diisopropylethylamine (8.0 mL), and NMP (25 mL) was stirred at 110° C. for 4 hours. To the reaction solution were added cesium carbonate (6.4 g) and 2-fluoro-5-(trifluoromethyl)pyridine (2.0 mL), and the mixture was stirred at 110° C. for 2 hours. The reaction mixture was cooled to room temperature, and ethyl acetate and water were added thereto to separate layers. The organic layer was washed with water, dried over sodium sulfate, and then concentrated in vavuo. The obtained residue was purified by silica gel column chromatography (eluting solution:hexane/ethyl acetate=1/1) to give Compound 42 (3.7 g).

Step (ii):

To a solution of Compound 42 (1.5 g) in methanol (20 mL) were added formic acid (1.5 mL), trimethyl orthoformate (11.0 mL), and zinc powder (1.3 g), and the mixture was stirred at room temperature for 1 hour. The reaction solution was filtrated with Celite and concentrated in vavuo. Ethyl acetate and aqueous Rochelle salt were added to the residue to separate layers. The organic layer was washed with water, dried over sodium sulfate, and then concentrated in vavuo. The obtained residue was purified by silica gel column chromatography (eluting solution:chloroform/methanol=20/1). The obtained crude product was recrystallized with heptane/2-propanol (=1/1) to give 2-methyl-1-(6-{[5-(trifluoromethyl)pyridin-2-yl]oxy}-1H-benzimidazol-1-yl) (1,1-$^2$H$_2$)propan-2-ol (650 mg).

$^1$H-NMR (DMSO-d6) δ: 1.07 (6H, s), 4.72 (1H, s), 7.00 (1H, dd, J=8.5, 2.4 Hz), 7.17 (1H, d, J=9.2 Hz), 7.56 (1H, d, J=2.4 Hz), 7.65 (1H, d, J=8.5 Hz), 8.13 (1H, s), 8.20 (1H, dd, J=9.2, 2.4 Hz), 8.55 (1H, d, J=2.4 Hz).

Example 3: Preparation of 4-[6-(4-chlorophenoxy)-1H-benzimidazol-1-yl]-2-methyl(4,4-$^2$H$_2$)butan-2-ol

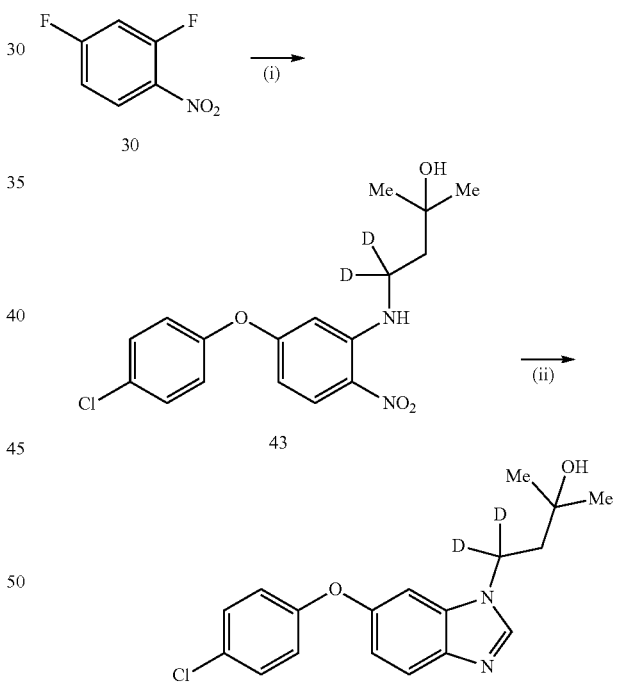

Step (i):

A mixture of 2,4-difluoro-1-nitrobenzene (Compound 30, 149 mg), a crude product of Compound 11 (Reference example 3) (235 mg), diisopropylethylamine (212 μL), and NMP (2.0 mL) was stirred at room temperature for 1 hour. Cesium carbonate (457 mg) and 4-chlorophenol (156 mg) were added to the reaction mixture, and the mixture was stirred at 150° C. for 1 hour. The reaction mixture was cooled to room temperature, and ethyl acetate and water were added thereto to separate layers. The organic layer was washed with water, dried over sodium sulfate, and concentrated in vavuo. The obtained residue was purified by silica gel column chromatography (eluting solution:hexane/ethyl acetate=1/1) to give Compound 43 (276 mg).

Step (ii):

To a solution of Compound 43 (276 mg) in methanol (4.0 mL) were added formic acid (0.3 mL), trimethyl orthoformate (1.7 mL), and zinc powder (256 mg), and the mixture was stirred at room temperature for 1 hour. The reaction solution was filtrated with Celite and concentrated in vavuo. The obtained residue was purified by silica gel column chromatography (eluting solution:chloroform/methanol=20/1). The crude product was slurry-washed with hexane/ethyl acetate (=1:1) to give 4-[6-(4-chlorophenoxy)-1H-benzimidazol-1-yl]-2-methyl(4,4-$^2$H$_2$)butan-2-ol (186 mg).

$^1$H-NMR (DMSO-d6) δ: 1.13 (6H, s), 1.84 (2H, s), 4.47 (1H, s), 6.91 (1H, dd, J=8.5, 2.4 Hz), 6.95-6.99 (2H, m), 7.33 (1H, d, J=2.4 Hz), 7.36-7.41 (2H, m), 7.66 (1H, d, J=8.5 Hz), 8.23 (1H, s).

Example 4: Preparation of 3-[{6-[4-(trifluoromethoxy)phenoxy]-1H-benzimidazol-1-yl}($^2$H$_2$)methyl]oxetan-3-ol

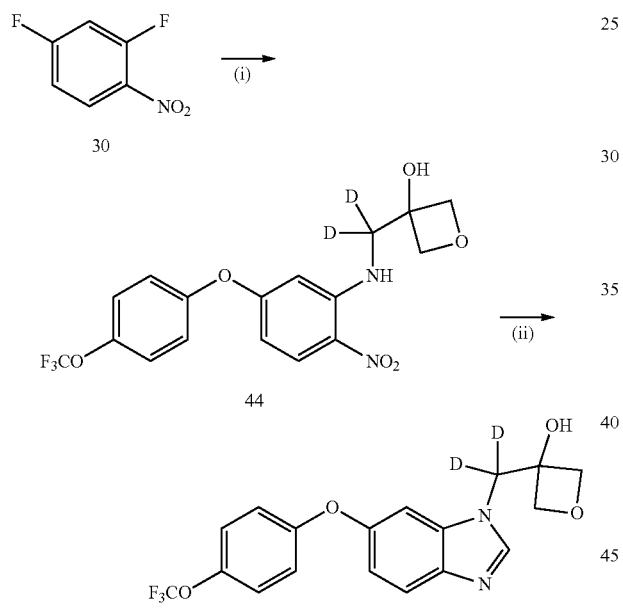

Step (i):

A mixture of 2,4-difluoro-1-nitrobenzene (Compound 30, 261 mg), a crude product of Compound 14 (Reference example 4) (632 mg), diisopropylethylamine (372 μL), and NMP (3.0 mL) was stirred at room temperature for 2 hours. Cesium carbonate (801 mg) and 4-(trifluoromethoxy)phenol (317 μL) were added to the reaction mixture, and the mixture was stirred at 120° C. for 2 hours. The reaction mixture was cooled to room temperature, and ethyl acetate and water were thereto. The organic layer was washed with water, dried over sodium sulfate, and concentrated in vavuo. The obtained residue was purified by silica gel column chromatography (eluting solution:chloroform/methanol=20/1) to give Compound 44 (353 mg).

Step (ii):

To a solution of Compound 44 (353 mg) in methanol (4.0 mL) were added formic acid (0.3 mL), trimethyl orthoformate (1.9 mL), and zinc powder (287 mg), and the mixture was stirred at room temperature for 2 hours. The reaction solution was filtrated with Celite, and concentrated in vavuo. The obtained residue was purified by silica gel column chromatography (eluting solution:chloroform/methanol=20/1). The crude product was slurry-washed with hexane/ethyl acetate (=1:1) to give 3-[{6-[4-(trifluoromethoxy)phenoxy]-1H-benzimidazol-1-yl}($^2$H$_2$)methyl]oxetan-3-ol (206 mg).

$^1$H-NMR (DMSO-d6) δ: 4.37-4.49 (4H, m), 6.18 (1H, s), 6.94 (1H, dd, J=8.5, 2.4 Hz), 7.02-7.06 (2H, m), 7.34 (2H, d, J=9.1 Hz), 7.48 (1H, d, J=2.4 Hz), 7.65 (1H, d, J=8.5 Hz), 8.26 (1H, s).

Example 5: Preparation of 3-[{6-[2-methoxy-4-(trifluoromethyl)phenyl]-1H-benzimidazol-1-yl}($^2$H$_2$)methyl]oxetan-3-ol

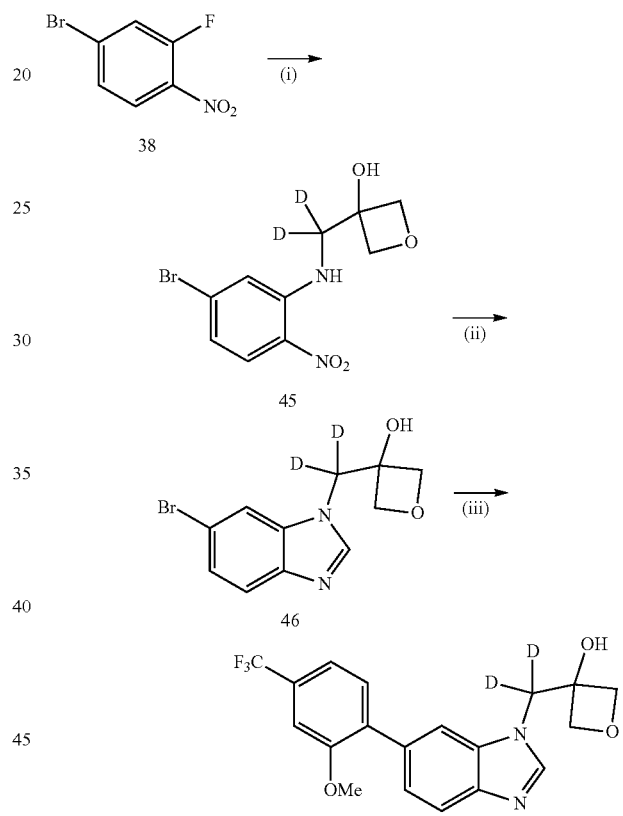

Step (i):

A mixture of 4-bromo-2-fluoro-1-nitrobenzene (Compound 38, 228 mg), a crude product of Compound 14 (Reference example 4) (770 mg), diisopropylethylamine (272 μL), and NMP (2.0 mL) was stirred at room temperature for 3 hours. Ethyl acetate and water were added to the reaction mixture to separate layers. The organic layer was washed with water, dried over sodium sulfate, and concentrated in vavuo. The obtained residue was purified by silica gel column chromatography (eluting solution:chloroform/methanol=20/1) to give Compound 45 (275 mg).

Step (ii):

To a solution of Compound 45 (275 mg) in methanol (9.0 mL) were added formic acid (0.3 mL), trimethyl orthoformate (2.0 mL), and zinc powder (295 mg), and the mixture was stirred at room temperature for 1 hour. The reaction solution was filtrated with Celite, and concentrated in vavuo. The obtained residue was purified by silica gel column chromatography (eluting solution:chloroform/methanol=20/1) to give Compound 46 (184 mg).
Step (iii):
A mixture of Compound 46 (184 mg), 2-methoxy-4-(trifluoromethyl)phenylboronic acid (213 mg), tetrakis(triphenylphosphine)palladium (75 mg), potassium carbonate (268 mg), 1,4-dioxane (4.5 mL), and distilled water (1.5 mL) was stirred at 100° C. for 2 hours. The reaction solution was cooled to room temperature, charged on silica gel and purified by silica gel column chromatography (eluting solution:chloroform/methanol=20/1). The obtained crude product was slurry-washed with hexane/ethyl acetate (=1/1) to give 3-[{6-[2-methoxy-4-(trifluoromethyl)phenyl]-1H-benzimidazol-1-yl}($^2H_2$)methyl]oxetan-3-ol (153 mg).
$^1$H-NMR (DMSO-d6) δ: 3.84 (3H, s), 4.41-4.55 (4H, m), 6.22 (1H, s), 7.33 (1H, dd, J=8.5, 1.8 Hz), 7.37-7.41 (2H, m), 7.55 (1H, d, J=7.9 Hz), 7.66 (1H, d, J=8.5 Hz), 7.84 (1H, d, J=1.2 Hz), 8.28 (1H, s).

Test 1: Measurement of Na Ion Current in Voltage-Dependent Na Channel Gene Expressed Cell
Nav 1.7 current was measured by automated patch clamp assay using cells stably-expressing human SCN9A.
Cells Stably-Expressing Human SCN9A
Tetracycline-induced cells stably-expressing SCN9A were obtained from ChanTest Corporation. The cells were passaged in Ham's F-12 medium containing 10% fetal bovine serum, 100 units/mL Penicillin-Streptomycin, 0.01 mg/mL Blasticidin, and 0.4 mg/mL Zeocin. The day before the measurement, the medium was replaced with Ham's F-12 medium containing 1 μg/mL tetracycline, 100 μmol/L sodium butyrate, 10% fetal bovine serum, and 100 units/mL Penicillin-Streptomycin. Next day, the Na ion current was measured by automated patch clamp assay.
Electrophysiologic Measurement of Na Ion Current
The Na ion current was measured by automated patch clamp assay using the following extracellular solution and intracellular solution.
Extracellular solution (mmol/L): NaCl 130, $MgCl_2$ 2, $CaCl_2$ 2, $CdCl_2$ 0.1, $NiCl_2$ 0.1, Tetraethylammonium-Cl 18, 4-aminopyridine 1, HEPES 10, (adjusting pH 7.4 with NaOH)
Intracellular solution (mmol/L): CsF 120, EGTA 10, NaCl 15, HEPES 10, (adjusting pH 7.2 with CsOH)
The control of the stimulating pulse and the data acquisition were carried out using EPC10 amplifier and Patch Master Software (HEKA). Data were sampled at 10 kHz, and low-pass filtered at 3 kHz. All the measurements were carried out at room temperature. The holding potential was set at a potential inactivating 50% Nav 1.7 channel (around −60 mV), and depolarizing pulse of 20 milliseconds (+10 mV) was given once. The inhibitory rate of the test compounds was calculated based on the results of cells whose peak current was 500 pA or more when the depolarizing pulse was given and whose whole-cell parameter did not greatly vary until the end of the data acquisition. The inhibitory rate of the Na ion current by the test compounds was calculated according to the following calculating formula with the peak current value generated by the depolarizing pulse.

Inhibitory rate of Na ion current (%)=100×[(Peak current value in the absence of Test Compound)−(Peak current value in the presence of Test Compound)]/(Peak current value in the absence of Test Compound)

Result:
The inhibitory rate of Na ion current by Example compounds 1 to 5 was evaluated. The results showed that the compounds of the present invention exhibit the inhibitory effect for Nav 1.7. The inhibitory rate (%) wherein the concentration of each compound is 10 μmol/L is shown in the following table.

| Example | Inhibitory rate (%) | Example | Inhibitory rate (%) | Example | Inhibitory rate (%) |
|---|---|---|---|---|---|
| 1 | 36 | 2 | 36 | 3 | 40 |
| 4 | 68 | 5 | 55 | | |

Test 2: Evaluation of Analgesic Effect in Streptozotocin-Induced Diabetic Peripheral Neuropathic Pain Models
Using some typical compounds among the compounds of the present invention, the inhibitory effect for neuropathic pain was determined through the evaluation of analgesic effect in rats streptozotocin (STZ)-induced diabetic peripheral neuropathy model.
The disease animal model was prepared by means of a partially-modified method of Fox et al. (Pain 81, 307-316, 1999). STZ was intraperitoneally administered to 9-week old male Wistar rats in 45 mg/kg of body weight to prepare animal model suffering from diabetic peripheral neuropathy.
The analgesic effect was evaluated by von Frey test. Specifically, mechanical sensitivity was measured by applying hairs (von Frey hair) to the plantar surface of the animal's hind paw, and then the reaction thresholds (50% paw withdrawal thresholds) for the mechanical stimulation was determined by using a formula based on Chaplan et al. (Journal of Neuroscience Methods 53, 55-63, 1994).
It was already confirmed in a preliminary study that the reaction thresholds of the animal's hind paw markedly decreased on the 21st day or later after administering STZ, hence the evaluation of the analgesic effect using the test compounds was done on any one day between the 21st day and the 30th day after administering STZ. One and two days before evaluating the test compounds, the reaction thresholds were measured to obtain an average thereof, and the average value was used as a reference value obtained before the test compounds would be administered.
In order to reduce the variations of the averaged values among the test groups and the measured values in each group, the animals were divided into 4 to 5 groups.
In the evaluation test of the test compounds, the reaction thresholds were measured after administering each test compound. One hour before measuring the reaction thresholds, each test compound was orally administered in 3 mg/kg of body weight. The strength of analgesic effect of each test compound is expressed as the extension width (g) of reaction thresholds which is obtained by the calculation formula of (reaction threshold obtained after administering test compound)−(reaction threshold obtained before administering test compound).
Result:
The extension width of reaction threshold in the compound of Example 2 was 5.0 g. The extension width in the solvent-administration group of the present test was 0.1 g.
The above result indicated that the compounds of the present invention exhibit good analgesic effects when the compounds are orally administered to rat models of diabetic peripheral neuropathy.
Test 3: Metabolic Stability Test in Liver Microsome
To a solution obtained by mixing 4 μL of human or rat liver microsome (produced by Xenotech, 20 mg/mL), 100 μL of 100 mM phosphate buffer solution (pH 7.4), and 74 μL of ultrapure water were added 2 μL of 1 μM DMSO solution of the test compound and further 40 μL of 10 mM aqueous NADPH (produced by Oriental Yeast Co., ltd.), and then the mixture was incubated at 37° C. for 30 minutes. After the incubation, 50 μL of the reaction solution was added to methanol to cease the metabolic reaction. The quenched solution was centrifuged at 4° C. at 4500 rpm for 5 minutes, and the supernatant was filtrated. 100 μL of the supernatant was mixed with 100 μL of 10 mM aqueous ammonium acetate, and the mixture was analyzed with LC (Shimadzu, NexeraX2)-MS (AB Sciex, TripleTOF5600) to determine the amount of the corresponding metabolite product in the mixture.

Result:

As for the compounds prepared in Comparative examples 1-3 and Examples 1-3, the corresponding metabolite products (Reference example 5-7) were assayed. The results showed that the rate of generating the metabolite product of each Example compound was lower than that of each Comparative example compound. Each rate of generating each metabolite product (pmol/min/mg protein) is shown in the following table.

| Comparative example/Example | Rate of generating the metabolite product (pmol/min/mg protein) | |
| --- | --- | --- |
| | human | rat |
| 1/1 | 0.045/n.d. | 0.262/n.d. |
| 2/2 | 0.204/0.026 | 2.52/0.260 |
| 3/3 | 0.756/0.069 | 3.30/0.40 | n.d.: not detect dealkyl metabolite product

Test 4: Rat Pharmacokinetic Study

The test compound was suspended in 0.5% aqueous methylcellulose, administered to a male rat (Crl: CD (SD)) in a dose of 3 mg/5 mL/kg. The blood collection was carried out 0.25, 0.5, 1, 2, 4, 6, and 24 hours after the administration. The blood collection (each 0.4 mL) was carried out with a syringe containing 4 μL of NOVO HEPARIN. The sampled blood was transferred to a cold tube for centrifugation, and centrifuged at 4° C. at 3000 rpm×10 min to prepare a plasma. To 50 μL of the prepared plasma was added methanol, and the mixture was stirred with Vortex mixer, and then centrifugated at 4° C. at about 9100×g for 5 minutes. 150 μL the supernatant was mixed with 300 μL of water, and the mixture was centrifugated at 4° C. at about 1800×g for 5 minutes. The supernatant was analyzed with LC (Shimadzu, A series)-MS (AB Sciex, API4000) to determine the amount of the corresponding metabolite product.

Result:

As for the compounds prepared in Comparative examples 2 and 3 and Examples 2 and 3, each concentration of the metabolite products after the administration to a male rat was assayed. The results showed that the exposure of the corresponding metabolite product (Reference example 6 and 7) of each Example compound was smaller than that of each Comparative example compound. Each pharmacokinetic parameter of metabolite products is shown in the following table, wherein $C_{max}$ denotes a maximum plasma concentration, and AUC denotes an area under the curve of plasma concentration-time from 0 to 24 hours.

| Comparative example/Example | $C_{max}$ (ng/mL) | AUC (ng/h/mL) |
| --- | --- | --- |
| 2/2 | 52.0/4.8 | 131/19.0 |
| 3/3 | 12.4/7.0 | 56.1/32.2 |

INDUSTRIAL APPLICABILITY

The compounds of the present invention can be used as a useful medicament for treating a disease involving Nav 1.7, for example, neuropathic pain, nociceptive pain, inflammatory pain, small-fiber neuropathy, erythromelalgia, paroxysmal extreme pain disorder, dysuria, and multiple sclerosis. Thus, the compounds of the present invention can be very useful pharmaceuticals.

The invention claimed is:

1. A compound of formula (I):

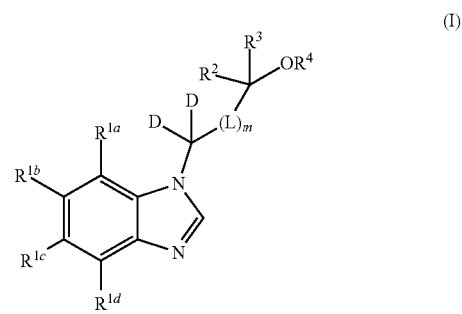

or a pharmaceutically acceptable salt thereof, wherein
$R^{1a}$, $R^{1b}$, $R^{1c}$ and $R^{1d}$ are independently hydrogen, halogen, cyano, $C_{1-4}$ alkyl, $C_{1-4}$ alkoxy, $C_{1-4}$ alkylamino (wherein the alkyl and the alkyl moiety in the alkoxy and the alkylamino may be independently substituted with 1 to 5 substituents selected independently from the group consisting of halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), $C_{3-7}$ cycloalkyl, $C_{3-7}$ cycloalkoxy, $C_{3-7}$ cycloalkylamino (wherein the cycloalkyl and the cycloalkyl moiety in the cycloalkoxy and the cycloalkylamino may be independently substituted with 1 to 5 substituents selected independently from the group consisting of halogen, hydroxy group, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), $C_{6-10}$ aryl, $C_{6-10}$ aryloxy, 5- to 12-membered heteroaryl, or 5- to 12-membered heteroaryloxy (wherein the aryl and the aryl moiety in the aryloxy, and the heteroaryl and the heteroaryl moiety in the heteroaryloxy may be independently substituted with 1 to 5 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, 3- to 7-membered non-aromatic heterocyclyl optionally-substituted with 1 to 3 substituents selected independently from Substituent-group B, $C_{1-4}$ alkylthio optionally-substituted with 1 to 3 substituents selected independently from Substituent-group A, and $C_{1-4}$ alkylsulfonyl optionally-substituted with 1 to 3 substituents selected independently from Substituent-group A), provided that at least one of $R^{1a}$, $R^{1b}$, $R^{1c}$ and $R^{1d}$ is the above $C_{6-10}$ aryl, $C_{6-10}$ aryloxy, 5- to 12-membered heteroaryl or 5- to 12-membered heteroaryloxy, $R^2$ and $R^3$ are independently hydrogen, $C_{1-6}$ alkyl (which may be independently substituted with 1 to 5 substituents selected independently from the group consisting of cyano, halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), or $C_{3-10}$ cycloalkyl, $R^4$ is hydrogen, $C_{1-6}$ alkyl (which may be substituted with 1 to 3 substituents selected independently from the group consisting of halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), or $C_{3-7}$ cycloalkyl (which may be independently substituted with 1 to 3 substituents selected independently from the group consisting of halogen, hydroxy group, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), m is 0, 1, or 2, L is $CR^7R^8$ provided that when m is 2, each $CR^7R^8$ is independently the same or different, $R^7$ and $R^8$ are independently hydrogen, hydroxy group, $C_{1-4}$ alkyl, $C_{1-4}$ alkoxy (wherein the alkyl and the alkyl moiety in the alkoxy may be independently substituted with 1 to 3 substituents selected independently from the group consisting of halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), $C_{3-7}$ cycloalkyl, or $C_{3-7}$ cycloalkoxy (wherein the cycloalkyl and the cycloalkyl moiety in the cycloalkoxy may be independently substituted with 1 to 3 substituents selected independently from the group consisting of halogen, hydroxy group, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), or in $R^2$, $R^3$ and —$OR^4$, $R^2$ and $R^3$ may be combined together with the carbon atom to which they are attached to form the following group of formula (II) with —$OR^4$

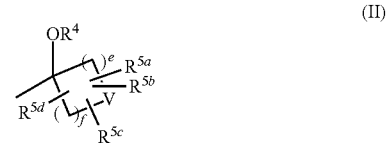

(II)

in formula (II), e and f are independently 1, 2 or 3, $R^4$ is as defined above, V is single bond or oxygen atom, $R^{5a}$, $R^{5b}$, $R^{5c}$, and $R^{5d}$ are independently hydrogen, halogen, hydroxy group, $C_{1-4}$ alkyl, or $C_{1-4}$ alkoxy, wherein the alkyl and the alkyl moiety in the alkoxy may be independently substituted with 1 to 3 substituents selected independently from the group consisting of halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, Substituent-group A is independently halogen, hydroxy group, $C_{1-4}$ alkoxy, $C_{3-7}$ cycloalkyl, or $C_{3-7}$ cycloalkoxy, Substituent-group B is independently halogen, hydroxy group, $C_{1-4}$ alkyl, $C_{1-4}$ alkoxy, $C_{3-7}$ cycloalkyl, or $C_{3-7}$ cycloalkoxy, and further any 1 to 6 hydrogen atoms in the compound of formula (I) may be replaced with deuterium atoms.

2. The compound of claim 1 or a pharmaceutically acceptable salt thereof, wherein $R^{1a}$, $R^{1b}$, $R^{1c}$ and $R^{1d}$ are independently, hydrogen, halogen, cyano, $C_{1-4}$ alkyl, $C_{1-4}$ alkoxy (wherein the alkyl and the alkyl moiety in the alkoxy may be independently substituted with 1 to 3 the same or different halogen atoms), $C_{6-10}$ aryl, $C_{6-10}$ aryloxy, 5- to 12-membered heteroaryl, or 5- to 12-membered heteroaryloxy (wherein the aryl and the aryl moiety in the aryloxy, and the heteroaryl and the heteroaryl moiety in the heteroaryloxy may be independently substituted with 1 to 3 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, and C$_{1-4}$ alkylsulfonyl optionally-substituted with 1 to 3 substituents selected independently from Substituent-group A).

3. The compound of claim 1 or a pharmaceutically acceptable salt thereof, wherein R$^{1a}$, R$^{1b}$, R$^{1c}$, and R$^{1d}$ are independently, hydrogen, C$_{6-10}$ aryl, C$_{6-10}$ aryloxy, 5- to 12-membered heteroaryl, or 5- to 12-membered heteroaryloxy, wherein the aryl and the aryl moiety in the aryloxy, and the heteroaryl and the heteroaryl moiety in the heteroaryloxy may be independently substituted with 1 to 3 substituents selected independently from the group consisting of halogen, C$_{1-4}$ alkyl optionally-substituted with 1 to 3 substituents selected independently from Substituent-group A, and C$_{1-4}$ alkoxy optionally-substituted with 1 to 3 substituents selected independently from Substituent-group A.

4. The compound of claim 1 or a pharmaceutically acceptable salt thereof, wherein R$^{1a}$ and R$^{1d}$ are hydrogen.

5. The compound of claim 1 or a pharmaceutically acceptable salt thereof, wherein R$^{1b}$ or R$^{1c}$ is C$_{6-10}$ aryl, C$_{6-10}$ aryloxy, 5- to 12-membered heteroaryl, or 5- to 12-membered heteroaryloxy (wherein the aryl and the aryl moiety in the aryloxy, and the heteroaryl and the heteroaryl moiety in the heteroaryloxy may be independently substituted with 1 to 3 substituents selected independently from the group consisting of halogen, C$_{1-4}$ alkyl optionally-substituted with 1 to 3 substituents selected independently from Substituent-group A, and C$_{1-4}$ alkoxy optionally-substituted with 1 to 3 substituents selected independently from Substituent-group A).

6. The compound of claim 1 or a pharmaceutically acceptable salt thereof, wherein R$^{1a}$, R$^{1c}$, and R$^{1d}$ are hydrogen.

7. The compound of claim 1 or a pharmaceutically acceptable salt thereof, wherein R$^{1b}$ is C$_{6-10}$ aryl, C$_{6-10}$ aryloxy, 5- to 12-membered heteroaryl, or 5- to 12-membered heteroaryloxy (wherein the aryl and the aryl moiety in the aryloxy, and the heteroaryl and the heteroaryl moiety in the heteroaryloxy may be independently substituted with 1 to 3 substituents selected independently from the group consisting of halogen, C$_{1-4}$ alkyl optionally-substituted with 1 to 3 substituents selected independently from Substituent-group A, and C$_{1-4}$ alkoxy optionally-substituted with 1 to 3 substituents selected independently from Substituent-group A).

8. The compound of claim 1 or a pharmaceutically acceptable salt thereof, wherein R$^2$ and R$^3$ are independently hydrogen or C$_{1-6}$ alkyl which may be independently substituted with 1 to 5 substituents selected independently from the group consisting of cyano, halogen, hydroxy group, and C$_{1-4}$ alkoxy optionally-substituted with 1 to 3 substituents selected independently from Substituent-group A, provided that both of R$^2$ and R$^3$ are not hydrogen, or R$^2$ and R$^3$ may be combined together with the carbon atom to which they are attached to form the following group of formula (IIa) with —OR$^4$

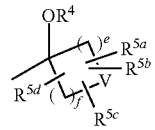

(IIa)

in formula (IIa), e and f are independently 1 or 2,

R$^4$ and V are as defined in claim 1, and

R$^{5a}$, R$^{5b}$, R$^{5c}$, and R$^{5d}$ are independently hydrogen or halogen.

9. The compound of claim 1 or a pharmaceutically acceptable salt thereof, wherein R$^2$ and R$^3$ are independently C$_{1-6}$ alkyl optionally-substituted with 1 to 5 the same or different halogen atoms, or R$^2$ and R$^3$ may be combined together with the carbon atom to which they are attached to form the following group of formula (IIb) with —OR$^4$

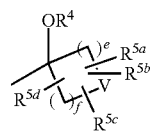

(IIb)

in formula (IIb), e and f are 1,

R$^4$ is hydrogen,

V is oxygen atom,

R$^{5a}$, R$^{5b}$, R$^{5c}$, and R$^{5d}$ are independently hydrogen or halogen.

10. The compound of claim 1 or a pharmaceutically acceptable salt thereof, wherein R$^2$ and R$^3$ are independently hydrogen or C$_{1-6}$ alkyl optionally-substituted with 1 to 5 the same or different halogen atoms, and R$^2$ and R$^3$ are not combined together with the carbon atom to which they are attached to form a ring.

11. The compound of claim 1 or a pharmaceutically acceptable salt thereof, wherein R$^2$ and R$^3$ may be combined together with the carbon atom to which they are attached to form the following group of formula (IIb) with —OR$^4$

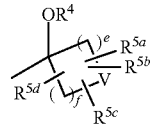

(IIb)

in formula (IIb), e and f are 1,

R$^4$ is hydrogen,

V is oxygen atom,

R$^{5a}$, R$^{5b}$, R$^{5c}$, and R$^{5d}$ are independently hydrogen or halogen.

12. The compound of claim 1 or a pharmaceutically acceptable salt thereof, wherein R⁴ is hydrogen, $C_{1-4}$ alkyl optionally-substituted with 1 to 3 the same or different halogen atoms, or $C_{3-7}$ cycloalkyl which may be substituted with 1 to 3 substituents selected independently from the group consisting of halogen, hydroxy group, and $C_{1-4}$ alkoxy optionally-substituted with 1 to 3 substituents selected independently from Substituent-group A.

13. The compound of claim 1 or a pharmaceutically acceptable salt thereof, wherein R⁴ is hydrogen.

14. The compound of claim 1 or a pharmaceutically acceptable salt thereof, wherein R⁷ and R⁸ are independently hydrogen or $C_{1-4}$ alkyl which may be substituted with 1 to 3 substituents selected independently from the group consisting of halogen, hydroxy group, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, and m is 0 or 1.

15. The compound of claim 1 or a pharmaceutically acceptable salt thereof, wherein R⁷ and R⁸ are hydrogen, and m is 0 or 1.

16. The compound of claim 1 or a pharmaceutically acceptable salt thereof, which is selected from the following compounds:
   6-(4-fluorophenoxy)-1H-benzimidazol-1-yl]-2-methyl(1,1-²H₂)propan-2-ol,
   2-methyl-1-(6-{[5-(trifluoromethyl)pyridin-2-yl]oxy}-1H-benzimidazol-1-yl)(1,1-²H₂)propan-2-ol,
   4-[6-(4-chlorophenoxy)-1H-benzimidazol-1-yl]-2-methyl(4,4-²H₂)butan-2-ol,
   3-[{6-[4-(trifluoromethoxy)phenoxy]-1H-benzimidazol-1-yl}(²H₂)methyl]oxetan-3-ol, and
   3-[{6-[2-methoxy-4-(trifluoromethyl)phenyl]-1H-benzimidazol-1-yl}(2H₂)methyl]oxetan-3-ol.

17. A pharmaceutical composition comprising the compound of claim 1 or a pharmaceutically acceptable salt thereof.

18. A pharmaceutical combination comprising the compound of claim 1 or a pharmaceutically acceptable salt thereof, and at least one drug selected from the group consisting of an antiepileptic agent, an antidepressive agent, a narcotic analgesic, an anti-inflammatory agent, a reductase inhibitor, and a prostaglandin derivative drug.

19. A method for treating neuropathic pain, nociceptive pain, inflammatory pain, small-fiber neuropathy, erythromelalgia, paroxysmal extreme pain disorder, dysuria, or multiple sclerosis, which comprises administering a therapeutically effective amount of the compound of claim 1 or a pharmaceutically acceptable salt thereof to a mammal in need thereof.

* * * * *